US010492958B2

(12) United States Patent
Matsui et al.

(10) Patent No.: US 10,492,958 B2
(45) Date of Patent: Dec. 3, 2019

(54) STRETCHABLE STRUCTURE WITH STRIPED ADHESIVE, METHOD FOR PRODUCING, AND ABSORBENT ARTICLE COMPRISING THE STRETCHABLE STRUCTURE

(71) Applicant: DAIO PAPER CORPORATION, Ehime (JP)

(72) Inventors: Tomotsugu Matsui, Ehime (JP); Yosuke Mori, Ehime (JP); Shunji Seno, Ehime (JP); Kento Fujima, Ehime (JP)

(73) Assignee: DAIO PAPER CORPORATION, Ehime (JP)

( * ) Notice: Subject to any disclaimer, the term of this patent is extended or adjusted under 35 U.S.C. 154(b) by 590 days.

(21) Appl. No.: 15/124,482

(22) PCT Filed: Mar. 20, 2015

(86) PCT No.: PCT/JP2015/058525
§ 371 (c)(1),
(2) Date: Sep. 8, 2016

(87) PCT Pub. No.: WO2015/151871
PCT Pub. Date: Oct. 8, 2015

(65) Prior Publication Data
US 2017/0014277 A1    Jan. 19, 2017

(30) Foreign Application Priority Data

Mar. 31, 2014 (JP) .................... 2014-071585
Mar. 12, 2015 (JP) .................... 2015-049179

(51) Int. Cl.
*A61F 13/15* (2006.01)
*A61F 13/496* (2006.01)
(Continued)

(52) U.S. Cl.
CPC .. *A61F 13/15593* (2013.01); *A61F 13/15707* (2013.01); *A61F 13/15739* (2013.01);
(Continued)

(58) Field of Classification Search
CPC ........ A61F 13/155593; A61F 13/15707; A61F 13/15793; A61F 13/49019; A61F 13/496;
(Continued)

(56) References Cited

U.S. PATENT DOCUMENTS

2010/0076394 A1* 3/2010 Hayase ............ A61F 13/15593
604/385.29
2010/0252178 A1* 10/2010 Takino ............. A61F 13/15593
156/164

(Continued)

FOREIGN PATENT DOCUMENTS

CN         102448418        5/2012
JP         2008-295930 A    12/2008
(Continued)

*Primary Examiner* — Kathryn E Ditmer
(74) *Attorney, Agent, or Firm* — Muncy, Geissler, Olds & Lowe, P.C.

(57) ABSTRACT

The present invention provides an underpants-type disposable diaper that has pleats formed in an outer body, which vertically and straightly extend, is excellent in appearance and air permeability, and is excellent in drawing preventing performance of a resilient and elastic member. The above-mentioned object is solved by a method for producing an underpants-type disposable diaper including, in forming stretchable regions, applying an adhesive to both an external surface of an inside layer and an internal surface of an outside layer in the same vertical striped pattern intermittent in an MD direction while transporting the inside layer and the outside layer, and then, fixing resilient and elastic members to the inside layer and the outside layer by bonding the inside layer and the outside layer to each other such that a position of the adhesive on the inside layer in the MD (Continued)

direction and a position of the adhesive on the outside layer in the MD direction are made to match with each other and sandwiching the resilient and elastic members between the inside layer and the outside layer continuously along the MD direction.

5 Claims, 24 Drawing Sheets

(51) Int. Cl.
  *A61F 13/49* (2006.01)
  *B32B 37/00* (2006.01)
(52) U.S. Cl.
  CPC ...... *A61F 13/496* (2013.01); *A61F 13/49019* (2013.01); *B32B 37/0076* (2013.01); *B32B 2307/728* (2013.01)
(58) Field of Classification Search
  CPC .. A61F 2013/49025; A61F 2013/49061; A61F 2013/49038; B32B 37/0076; B32B 37/1292
  See application file for complete search history.

(56) References Cited

U.S. PATENT DOCUMENTS

| | | | |
|---|---|---|---|
| 2011/0319853 A1* | 12/2011 | Yamashita | A61F 13/49011 604/385.3 |
| 2012/0095429 A1 | 4/2012 | Kobayashi et al. | |
| 2016/0106601 A1* | 4/2016 | Kobayashi | A61F 13/49058 604/385.16 |

FOREIGN PATENT DOCUMENTS

| | | | |
|---|---|---|---|
| JP | 2009-148447 A | | 7/2009 |
| JP | 2009148447 A | * | 7/2009 |
| JP | 2009-297096 A | | 12/2009 |
| JP | 2013-34850 A | | 2/2013 |
| JP | 2014-4115 A | | 1/2014 |
| WO | WO 2007/037390 A1 | | 4/2007 |
| WO | WO 2008/078610 A1 | | 7/2008 |
| WO | WO 2014/004941 A1 | | 1/2014 |
| WO | WO2014010340 A1 | | 1/2014 |

* cited by examiner

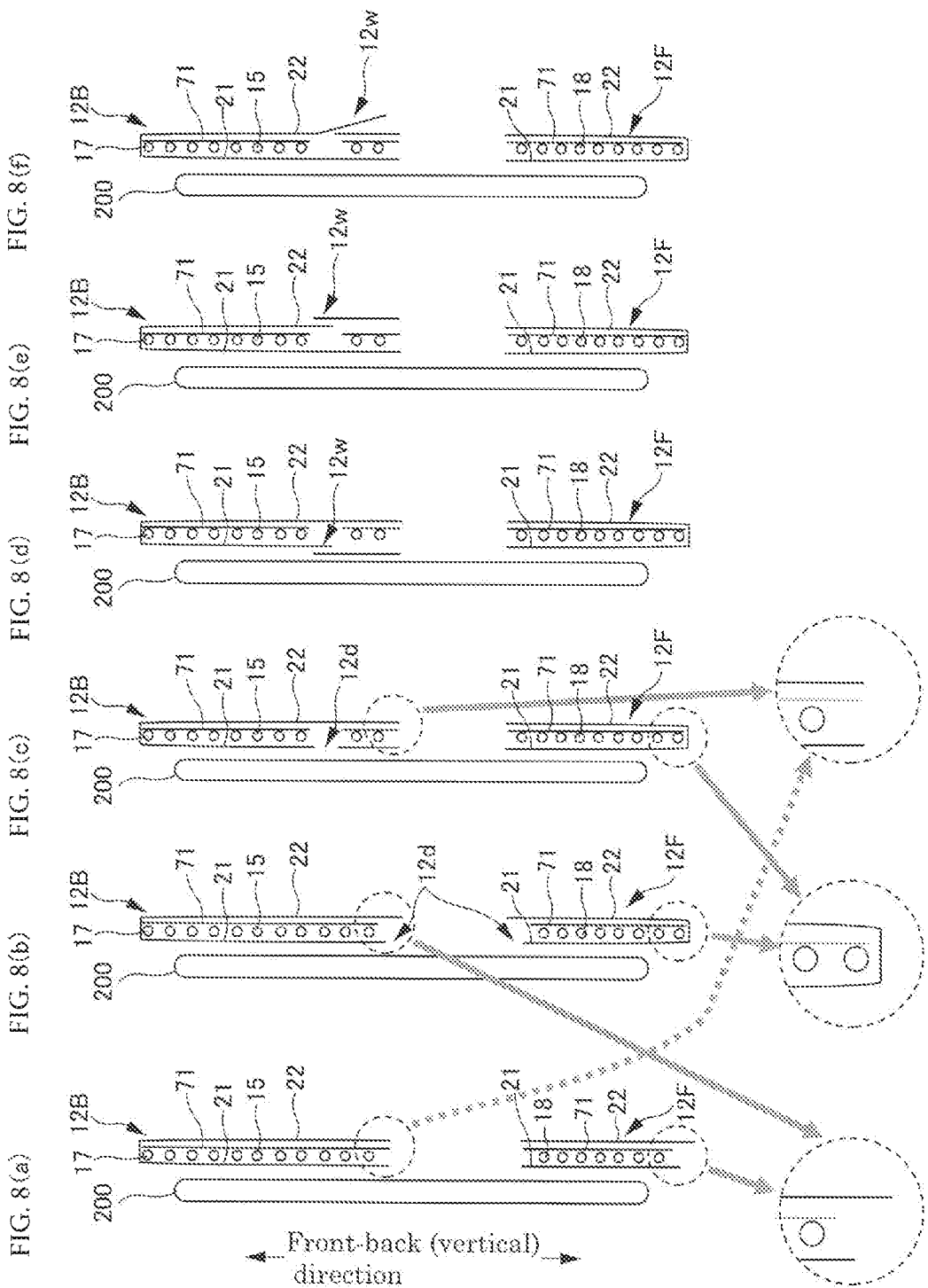

FIG.21
(Sample No. 13)
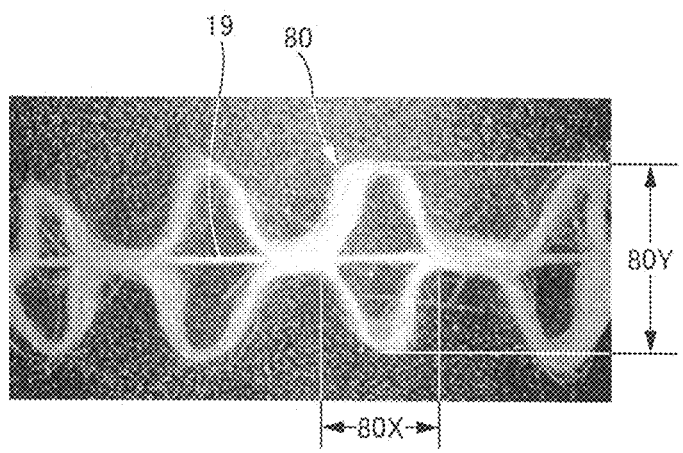
(Sample No. 14)
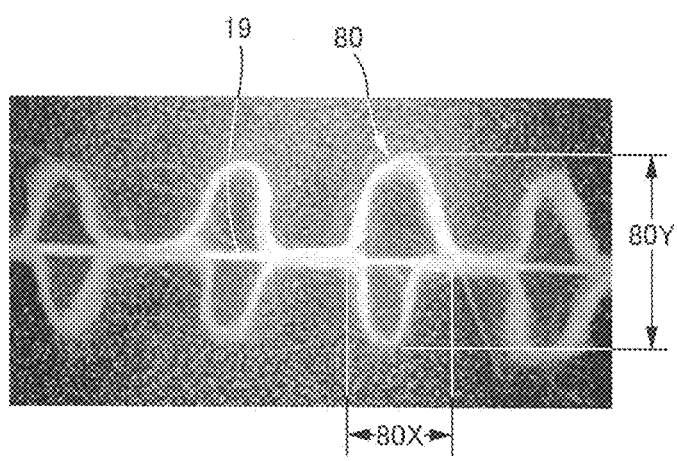

Extending direction

STRETCHABLE STRUCTURE WITH STRIPED ADHESIVE, METHOD FOR PRODUCING, AND ABSORBENT ARTICLE COMPRISING THE STRETCHABLE STRUCTURE

TECHNICAL FIELD

The present invention relates to a method for producing a stretchable structure for an absorbent article, a method for producing an underpants-type disposable diaper, and the underpants-type disposable diaper.

BACKGROUND ART

An underpants-type disposable diaper includes an outer body constituting a front panel and a back panel, and an inner body having an absorber and fixed to the internal surface of the outer body. Both side portions of the outer body in the front panel and both side portions of the outer body in the back panel are joined together to form a waist opening and a pair of right and left leg openings.

In the underpants-type disposable diaper, elongated resilient and elastic members such as rubber threads are fixed in an extended state at several sections of the outer body along a circumferential direction thereof to form a stretchable structure around the waist portion to enhance the fit to the human body. In particular, underpants-type disposable diapers are widely used, each of which includes waist-edge portion resilient and elastic members at the edge portion of the waist opening along the width direction and lower waist portion resilient and elastic members closer to the leg portions than to the waist-edge portion resilient and elastic members along the width direction, due to their relatively good fit to the human body.

As an improvement of the stretchable structure of the waist portion of the underpants-type disposable diaper, as illustrated in FIG. 22, there have been proposed stretchable structures where, two sheet materials 12H and 12S are intermittently joined together in a width direction and a vertical direction orthogonal to the width direction to form a large number of sheet joined sections 70, a large number of elongated resilient and elastic members 19 are arranged so as not to pass through the sheet joined sections 70 (so as to pass through non-joined sections) between the sheet materials 12H and 12S, and only both end portions of these resilient and elastic members 19 are fixed to both the sheet materials 12H and 12S (refer to Patent Documents 1 to 3. These stretchable structures will be hereinafter also referred to as vertical intermittent joined form). According to the related art, the vertically aligned sheet joined sections 70 form vertically continuous grooves, and the portions between the grooves form large pleats 80 that swell to the same extent on both the front and back sides. The grooves improve air permeability and the pleats 80 produce excellent softness. A reference numeral 75 in FIG. 22 indicates welded portions of the sheet materials 12H and 12S. Even when the sheet joined sections 70 are formed using an adhesive, the pleats 80 have the similar shape.

However, in the prior-art technology, the pleats make fluffy or wave-shaped pleats. Thus, there is a problem that the diaper is inferior in terms of appearance and air permeability.

In order to solve this problem, it has been considered that in providing the resilient and elastic member along the width direction on the waist portion of the outer body, a vertically continuous adhesive applied to any one of an inside layer facing the inner side of the resilient and elastic member and an outside layer facing the outer side thereof is used to bond the inside layer and the outside layer to each other intermittently in the width direction to form vertical striped sheet joined sections and the resilient and elastic members are bonded to the inside layer and the outside layer with the adhesive. In this form, the sheet joined sections are vertically continuous and the resilient and elastic members are fixed to only the sheet joined sections. Therefore, the portions between the sheet joined sections swell to the directions opposite to each other to form pleats. The pleats vertically and straightly extend and appearance and air permeability are excellent.

However, although the underpants-type disposable diaper produced by this production method is flexible because the adhesive is not continuous in the direction intersecting with the width direction at the inner side or the outer side of the resilient and elastic member, there has been a problem that fixing of the resilient and elastic member is insufficient and an end portion of the resilient and elastic member is easy to be drawn to the opposite side (hereinafter, also simply referred to as drawing). For solving this problem, increase in an adhesive application width, decrease in an adhesive application interval, and the like in regions including the end portion of the resilient and elastic member have been also considered. This however cannot avoid lowering in flexibility and change in appearance such as partial change of the shape of the pleats.

CITATION LIST

Patent Document

Patent Document 1: JP-A No. 2008-295930
Patent Document 2: JP-A No. 2009-297096
Patent Document 3: JP-A No. 2009-148447

SUMMARY OF INVENTION

Problem to be Solved by the Invention

A major object of the present invention is to provide an underpants-type disposable diaper having a pleat formed on an outer body, which vertically and straightly extends, excellent in appearance and air permeability, and excellent in drawing preventing performance of a resilient and elastic member, a method for producing a stretchable structure of an absorbent article, which is appropriate for production of the underpants-type disposable diaper, and a method for producing the underpants-type disposable diaper.

Means for Solving the Problem

The present invention as a solution to the foregoing problems is as follows:
<The Invention of Claim 1>
A method for producing a stretchable structure of an absorbent article,
the stretchable structure including a plurality of elongated resilient and elastic members provided with spaces left therebetween along an extending direction, and a first layer and a second layer facing one side and the other side of the resilient and elastic members, respectively, wherein
the first layer and the second layer are joined together with an adhesive applied in a striped pattern intermittent in the extending direction so as to form sheet joined sections, the resilient and elastic members are fixed to the first layer and the second layer with the adhesive at positions intersecting with the sheet joined sections, and the first layer and the second layer contract with contraction of the resilient and elastic members and portions of the first layer and the second layer between the sheet joined sections swell to directions opposite to each other so as to form pleats, the method comprising:

applying the adhesive to both an external surface of the first layer and an internal surface of the second layer in the same striped pattern intermittent in a MD direction while transporting the first layer and the second layer in the MD direction, and then, fixing the resilient and elastic members to the first layer and the second layer by bonding the first layer and the second layer to each other such that a position of the adhesive on the first layer in the MD direction and a position of the adhesive on the second layer in the MD direction are made to match with each other and sandwiching the resilient and elastic members between the first layer and the second layer continuously along the MD direction.

(Operation and Effect)

With the stretchable structure that is produced by the foregoing method, the adhesive is applied to both the surfaces of the first layer and the second layer in the same striped pattern (hereinafter, also referred to as double-sided application) and the first layer and the second layer are bonded to each other such that both the positions of the adhesive are made to match with each other. Therefore, the sheet joined sections are formed in the striped pattern orthogonal to the extending direction and portions located between the striped sheet joined sections swell to the directions opposite to each other so as to form the pleats. Accordingly, the formed pleats extend straightly in the direction orthogonal to the extending direction and appearance and air permeability are excellent. In addition, the resilient and elastic member is made to firmly adhere to both the first layer and the second layer in portions intersecting with the adhesive in the sheet joined sections. Therefore, drawing preventing performance of the resilient and elastic member is also excellent.

Furthermore, with the production method, when non-woven fabric is used as the first layer and the second layer, the MD direction of the non-woven fabric in producing the absorbent article naturally corresponds to the extending direction naturally. Therefore, bending resistance of the first layer and the second layer in the extending direction is higher than bending resistance thereof in the direction orthogonal to the extending direction. As a result, advantages that the formed pleats are easy to swell roundly, compression resilience thereof in the thickness direction is increased, and the pleats are difficult to lie down and become rich in softness when touched are provided. By contrast, when the bending resistance of the first layer and the second layer in the extending direction is lower than the bending resistance thereof in the direction orthogonal to the extending direction, the pleats are formed into thin acute shapes and are easy to lie down and the compression resilience thereof in the thickness direction is decreased. In order to improve them, the basis weight of the non-woven fabric that is used for the first layer and the second layer can be increased. However, the increase in the basis weight of the non-woven fabric causes a risk that stiff feeling is increased (stiffness is excessively increased) and the softness when touched is deteriorated even if softness in appearance is provided.

<The Invention of Claim 2>

The method for producing the stretchable structure of the absorbent article according to claim 1, wherein the first layer and the second layer are a one-side portion and another-side portion of one continuous belt-shaped sheet material, which is transported in the MD direction, relative to an intermediate position in a CD direction, and the adhesive is applied to both the external surface of the first layer and the internal surface of the second layer in the striped pattern such that the positions of the adhesive in the MD direction are the same, and then, the resilient and elastic members are fixed to the first layer and the second layer with the adhesive by folding back the sheet material in the CD direction to bond the first layer and the second layer to each other and sandwiching the resilient and elastic members between the first layer and the second layer.

(Operation and Effect)

When different sheet materials as the first layer and the second layer are transported and bonded to each other, the position of the adhesive on the first layer in the MD direction and the position of the adhesive on the second layer in the MD direction are easy to be deviated and positional adjustment for aligning the positions is complicated. By contrast, when the first layer and the second layer are formed as the one-side portion and the other-side portion of one continuous belt-shaped sheet material relative to the intermediate position in the CD direction and the continuous belt-shaped sheet material is folded back in the CD direction so as to bond the first layer and the second layer to each other after application of the adhesive, the position of the adhesive on the first layer in the MD direction and the position of the adhesive on the second layer in the MD direction are less deviated (no positional deviation is generated at sides of a folding line at least) even without positional adjustment (although the positional adjustment may be performed).

<The Invention of Claim 3>

The method for producing the stretchable structure of the absorbent article according to claim 1 or 2, wherein the position of the adhesive on the first layer in the MD direction and the position of the adhesive on the second layer in the MD direction are made to match with each other by dividing any one of the first layer and the second layer into a plurality of portions at intermediate positions in the CD direction and individually adjusting positions of these divided portions in the MD direction before the first layer and the second layer are bonded to each other.

(Operation and Effect)

When the widths (lengths in the CD direction) of the first layer and the second layer to be transported are large as described above, it is difficult to match the position of the adhesive on the first layer in the MD direction and the position of the adhesive on the second layer in the MD direction entirely in the CD direction. Therefore, the following is one preferable form. That is, the positional adjustment for matching the position of the adhesive on the first layer in the MD direction and the position of the adhesive on the second layer in the MD direction is made easy by dividing any one of the layers to decrease the width thereof before the first layer and the second layer are bonded to each other.

<The Invention of Claim 4>

A method for producing an underpants-type disposable diaper, the underpants-type disposable diaper including an outer body constituting a front panel and a back panel and an inner body having an absorber and fixed to an internal surface of the outer body, wherein both side portions of the outer body in the front panel and both side portions of the outer body in the back panel are joined together to form side seal portions, thereby forming a waist opening and a pair of right and left leg openings, and the outer body in at least one of the front and back panels includes an elongated resilient and elastic member along a width direction, an inside layer and an outside layer facing an inner side and an outer side of the resilient and elastic member, respectively, and sheet joined sections formed by joining the inside layer and the outside layer together with an adhesive applied in a vertical striped pattern intermittent in the width direction, and has stretchable regions in which the resilient and elastic member is fixed between the inside layer and the outside layer with the adhesive in portions intersecting with the sheet joined sections in a state of being extended in the width direction, and in the stretchable regions, the inside layer and the outside layer contract with contraction of the resilient and elastic member, so that portions of the inside layer and the outside layer, which are located between the sheet joined sections, swell to directions opposite to each other so as to form pleats, the method comprising:

in forming the stretchable regions, applying the adhesive to both an external surface of the inside layer and an internal surface of the outside layer in the same vertical striped pattern intermittent in a MD direction while transporting the inside layer and the outside layer in the MD direction, and then, fixing the resilient and elastic member to the inside layer and the outside layer with the adhesive by bonding the inside layer and the outside layer to each other such that a position of the adhesive on the inside layer in the MD direction and a position of the adhesive on the outside layer in the MD direction are made to match with each other and sandwiching the resilient and elastic member between the inside layer and the outside layer continuously along the MD direction.

(Operation and Effect)

In the above-mentioned stretchable regions, the adhesive is applied to both the surfaces of the inside layer and the outside layer in the same vertical striped pattern (hereinafter, also referred to as double-sided application) and the inside layer and the outside layer are bonded to each other such that both the positions of the adhesive are made to match with each other. Therefore, in the stretchable regions, the sheet joined sections are formed in the vertical striped pattern and portions located between the vertical striped sheet joined sections swell to the directions opposite to each other so as to form the pleats. Accordingly, the pleats formed in the stretchable regions vertically and straightly extend and appearance and air permeability are excellent. In addition, the resilient and elastic member in the stretchable regions is made to firmly adhere to both the inside layer and the outside layer in portions intersecting with the adhesive in the sheet joined sections. Therefore, drawing preventing performance of the resilient and elastic member is also excellent.

<The Invention of Claim 5>

The method for producing the underpants-type disposable diaper according to claim 4, wherein the underpants-type disposable diaper has a non-stretchable region formed in a region for fixing the inner body in the outer body, the stretchable regions are provided at respective sites between the non-stretchable region and the side seal portions at both sides in the width direction, and the inside layer and the outside layer are continuous from the stretchable region at one side in the width direction to the stretchable region at the other side through the non-stretchable region, in forming the stretchable regions and the non-stretchable region, the adhesive is applied to both the external surface of the inside layer and the internal surface of the outside layer in the same vertical striped pattern intermittent in the MD direction at sites corresponding to the stretchable regions while transporting the inside layer and the outside layer in the MD direction whereas the adhesive is applied to any one of the external surface of the inside layer and the internal surface of the outside layer in the vertical striped pattern continuous from the stretchable regions and the adhesive is not applied to the other of the external surface of the inside layer and the internal surface of the outside layer in the vertical striped pattern at a site corresponding to the non-stretchable region, and then, the resilient and elastic member is fixed to the inside layer and the outside layer with the adhesive by bonding the inside layer and the outside layer to each other such that the position of the adhesive on the inside layer in the MD direction and the position of the adhesive on the outside layer in the MD direction at the sites corresponding to the stretchable regions are made to match with each other and sandwiching the resilient and elastic member between the inside layer and the outside layer continuously along the MD direction, and subsequently, the resilient and elastic member only at the site corresponding to the non-stretchable region is finely cut in the MD direction.

(Operation and Effect)

In the underpants-type disposable diaper including the resilient and elastic member in the outer body, when the resilient and elastic member is provided in the region for fixing the inner body, the inner body is deformed in a contraction manner in the width direction with contraction force of the resilient and elastic member and appearance and the like are deteriorated in some cases. For this reason, the resilient and elastic member is attached continuously in the MD direction at the time of manufacturing but the resilient and elastic member is finely cut in the MD direction in substantially the entire region for fixing the inner body so as to form the non-stretchable region in which no contraction force act after attached, in general. In the non-stretchable region, the fine pieces of the resilient and elastic member after cut preferably contract without involving the inside layer and the outside layer and it is therefore sufficient that adhesion force of the resilient and elastic member is weak. Accordingly, in the non-stretchable region, it is also preferable that the adhesive be applied to only one of the external surface of the inside layer and the internal surface of the outside layer in the vertical striped pattern continuously from the stretchable regions and the adhesive is not applied to the other one in the vertical striped pattern (hereinafter, also referred to one-sided application) without performing the double-sided application unlike the foregoing manner. With this, reduction in the usage amount of the adhesive and improvement in flexibility of the non-stretchable region of the outer body can be also achieved.

<The Invention of Claim 6>

The method for producing the underpants-type disposable diaper according to claim 5, wherein before the resilient and elastic member is sandwiched between the inside layer and the outside layer continuously along the MD direction, the adhesive is applied to an outer circumferential surface of the resilient and elastic member in areas of the resilient and elastic member in the MD direction, which correspond to both end portions of the stretchable regions in the width direction.

(Operation and Effect)

In order to make the drawing preventing performance more excellent, the following is also a preferable form. That is, the adhesive is applied to the outer circumferential surface of the resilient and elastic member in the ranges thereof in the MD direction, which correspond to both the end portions of the stretchable regions in the width direction as described above.

<The Invention of Claim 7>

An underpants-type disposable diaper comprising an outer body constituting a front panel and a back panel and an inner body having an absorber and fixed to an internal surface of the outer body, both side portions of the outer body in the front panel and both side portions of the outer body in the back panel being joined together to form side seal portions, thereby forming a waist opening and a pair of right and left leg openings, the outer body in at least one of the front and back panels including an elongated resilient and elastic member along a width direction, an inside layer and an outside layer facing an inner side and an outer side of the resilient and elastic member, respectively, and sheet joined sections formed by joining the inside layer and the outside layer together with an adhesive applied in a vertical striped pattern intermittent in the width direction, and having stretchable regions in which the resilient and elastic member is fixed between the inside layer and the outside layer with the adhesive in portions intersecting with the sheet joined sections in a state of being extended in the width direction, and in the stretchable regions, the inside layer and the outside layer contracting with contraction of the resilient and elastic member, so that portions of the inside layer and the outside layer, which are located between the sheet joined sections, swelling to opposite directions so as to form pleats, wherein in the stretchable regions, the resilient and elastic member is fixed to the inside layer and the outside layer with the vertically continuous adhesive at both inner and outer sides of the resilient and elastic member in the portions in which the sheet joined sections and the resilient and elastic member intersect with each other.

(Operation and Effect)

In the above-mentioned stretchable regions, the sheet joined sections are formed in the vertical striped shape with the vertically continuous adhesive at both the inner and outer sides of the resilient and elastic member and portions located between the vertical striped sheet joined sections swell to the directions opposite to each other so as to form the pleats. Accordingly, the pleats formed in the stretchable regions vertically and straightly extend and appearance and air permeability are excellent. In addition, the resilient and elastic member in the stretchable regions is made to firmly adhere to both the inside layer and the outside layer with the vertically continuous adhesive at both the inner and outer sides of the resilient and elastic member in the portions intersecting with the adhesive in the sheet joined section. Therefore, drawing preventing performance of the resilient and elastic member is also excellent.

<The Invention of Claim 8>

The underpants-type disposable diaper according to claim 7, wherein the underpants-type disposable diaper has a non-stretchable region formed in a region for fixing the inner body in the outer body, the stretchable regions are provided at respective sites between the non-stretchable region and the side seal portions at both sides in the width direction, and the inside layer and the outside layer are continuous from the stretchable region at one side in the width direction to the stretchable region at the other side through the non-stretchable region, the non-stretchable region includes the resilient and elastic member finely cut in the width direction between the inside layer and the outside layer, and in the non-stretchable region, the adhesive is non-continuous vertically at any one side of inner and outer sides of the resilient and elastic member in the portions in which the sheet joined sections and the resilient and elastic member intersect with each other.

(Operation and Effect)

In the underpants-type disposable diaper including the resilient and elastic member in the outer body, when the resilient and elastic member is provided in the region for fixing the inner body, the inner body is deformed in a contraction manner in the width direction with contraction force of the resilient and elastic member and appearance and the like are deteriorated in some cases. For this reason, the resilient and elastic member is attached continuously in the MD direction (width direction in the case of a product) in attaching but the resilient and elastic member is finely cut in the MD direction (width direction in the case of the product) in substantially the entire region for fixing the inner body so as to form the non-stretchable region in which no contraction force act after attached, in general. In the non-stretchable region, the fine pieces of the resilient and elastic member after cut preferably contract without involving the inside layer and the outside layer and it is therefore sufficient that adhesion force of the resilient and elastic member is weak. Accordingly, in the non-stretchable region, it is also preferable that the adhesive be vertically non-continuous at any one side of the inner and outer sides of the resilient and elastic member in the portions in which the sheet joined sections and the resilient and elastic member intersect with each other as described above. With this, reduction in the usage amount of the adhesive and improvement in flexibility of the non-stretchable region of the outer body can be also achieved.

<The Invention of Claim 9>

The underpants-type disposable diaper according to claim 8, wherein in both end portions of the stretchable regions in the width direction, portions of the resilient and elastic member, which do not intersect with the sheet joined sections with the adhesive applied in the vertical striped pattern, are fixed to the inside layer and the outside layer with the adhesive applied to an outer circumferential surface of the resilient and elastic member.

(Operation and Effect)

In order to make the drawing preventing performance more excellent, the following is also a preferable form. That is, in both the end portions of the stretchable regions in the width direction, portions of the resilient and elastic member, which do not intersect with the sheet joined sections, are fixed to the inside layer and the outside layer with the adhesive applied to the outer circumferential surface of the resilient and elastic member as described above.

Advantageous Effects of Invention

As described above, the present invention produces advantages that pleats extend straightly, appearance and air permeability are excellent, and drawing preventing performance of a resilient and elastic member is excellent, and others.

BRIEF DESCRIPTION OF DRAWINGS

FIGS. 8 (a), (b), (c), (d), (e) and (f) are cross-sectional views of major components of the underpants-type disposable diaper;

FIG. 21 represents microscope photographs;

Figure 1:
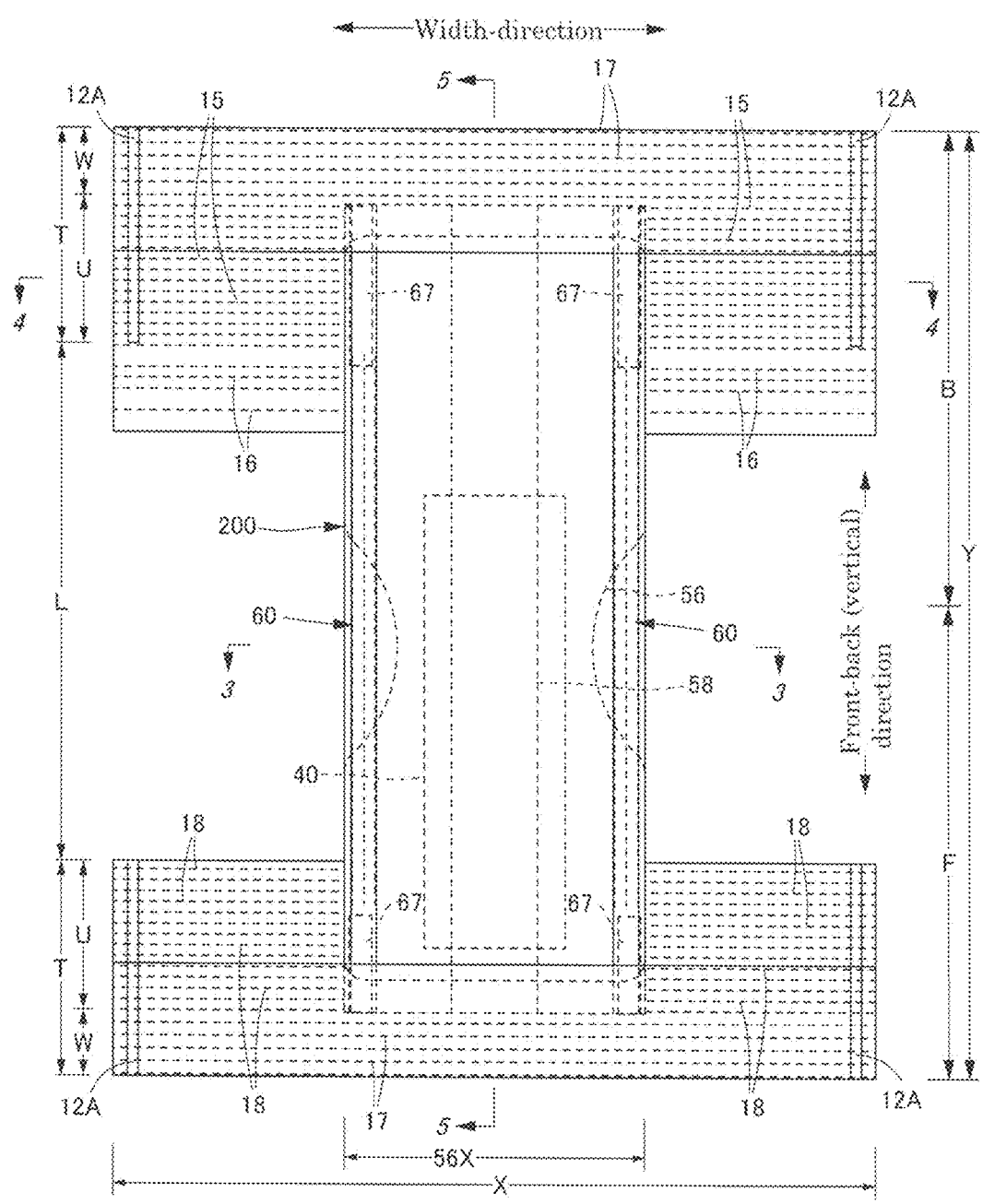
FIG. 1 is a planar view of an internal surface of an underpants-type disposable diaper in the open state.

An embodiment of the present invention will be described below with reference to the accompanying drawings.

<Underpants-Type Disposable Diaper>

FIGS. 1 to 7 illustrate one example of an underpants-type disposable diaper. In this underpants-type disposable diaper, both side edges of a ventral side outer body 12F in a width direction and both side edges of a dorsal side outer body 12B in the width direction are joined along a vertical direction by heat sealing, ultrasonic welding, or the like to form cylindrical-shaped outer bodies 12F and 12B. In addition, on the outer bodies 12F and 12B, a front end portion of an inner body 200 is connected by a hot-melt adhesive or the like to an inner surface of a central portion of the ventral side outer body 12F in the width direction, and a back end portion of the inner body 200 is connected by the hot-melt adhesive or the like to the inner surface of a central portion of the dorsal side outer body 12B in the width direction. Reference sign 12A indicates a joined section (side seal portion) of the ventral side outer body 12F and the dorsal side outer body 12B. In addition, reference sign Y indicates the entire length (vertical length from an edge of a waist opening in the front panel F to an edge of the waist opening in the back panel B) of the diaper in the open state, and reference sign X indicates the entire width of the diaper in the open state.

The inner body 200 is a part absorbing and retaining excretion such as urine, and the outer bodies 12F and 12B are parts for supporting the inner body 200 for the wearer's body. The dot patterns in the drawing represent a hot-melt adhesive for joining the constituent members. Alternatively, the members may be joined by welding process. The hot-melt adhesive may be applied in a solid, bead, curtain, summit, or spiral pattern. Instead of or in addition to this, for fixation of the resilient and elastic members, the hot-melt adhesive may be applied to the outer peripheral surface of the resilient and elastic members by the means of a comb gun or a Sure-Wrap application means.

Figure 2:
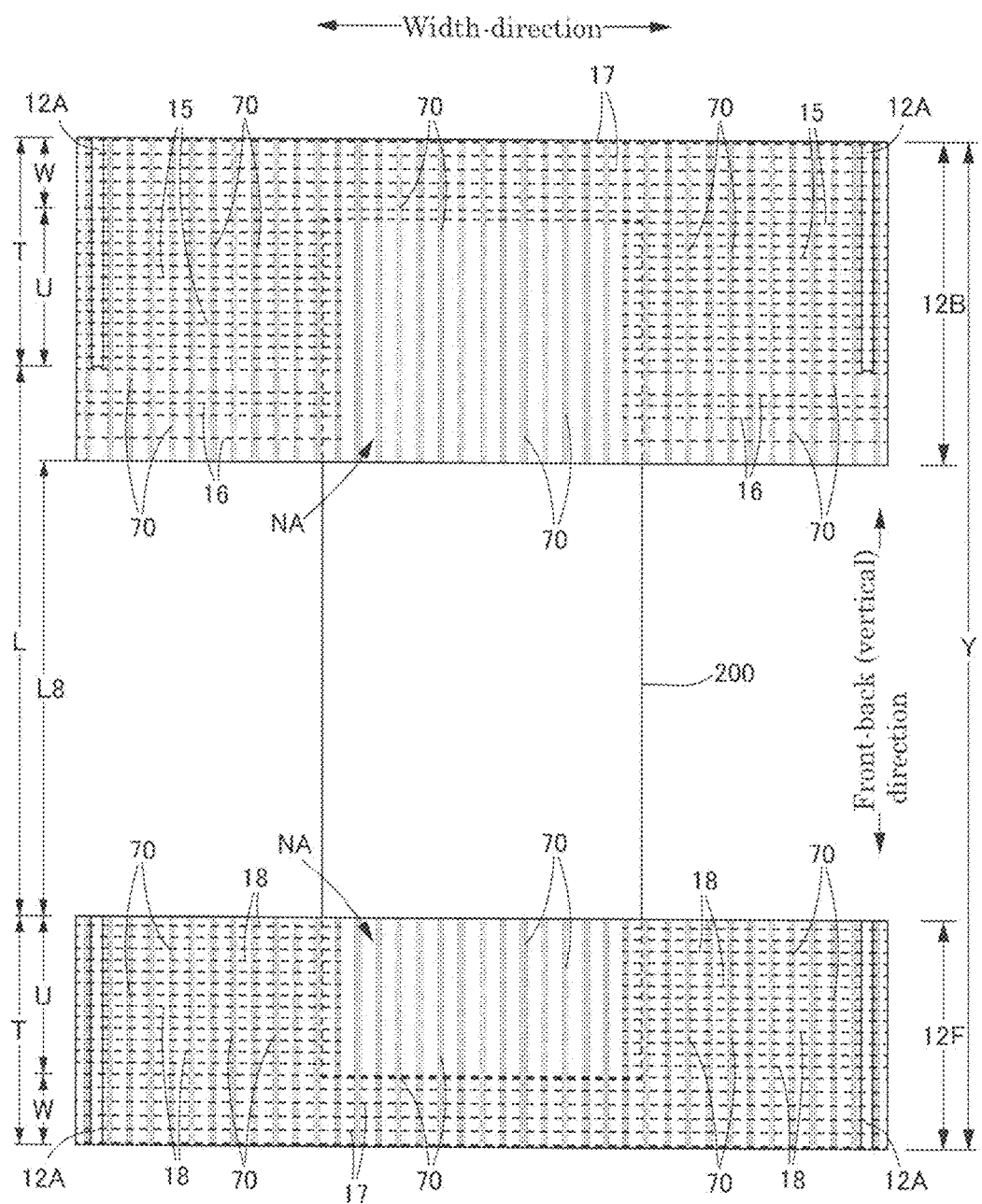
FIG. 2 is a planar view of an external surface of the underpants-type disposable diaper in the open state.

The upper opening of the outer bodies 12F and 12B constitutes a waist opening through which the wearer's waist is passed. Parts surrounded, respectively, by lower edges of the outer bodies 12F and 12B and side edges of the inner body 200 at both sides of the inner body 200 in the width direction constitute leg openings through which the wearer's legs are passed. With respective welded portions 12A taken off and the outer bodies 12F and 12B opened, the inner body 200 has a narrower shaped intermediate portion in the front-back direction, as illustrated in FIGS. 1 and 2. The inner body 200 extends from the dorsal side to the ventral side through the crotch portion so as to cover them. The inner body 200 is a portion receiving and absorbing excretion and retaining the liquid thereof, and the outer bodies 12F and 12B are portions to support the inner body 200 to the wearer.

(Inner Body)

Figure 3:
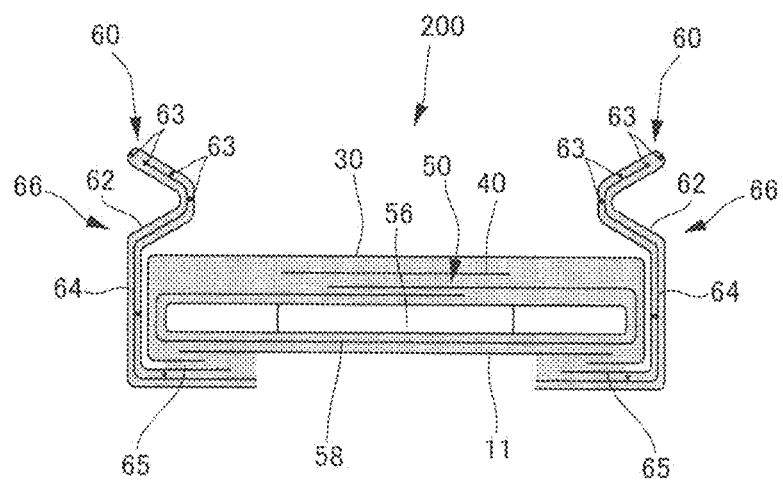
FIG. 3 is a cross-sectional view of FIG. 1 taken along line 3-3.
Figure 4:
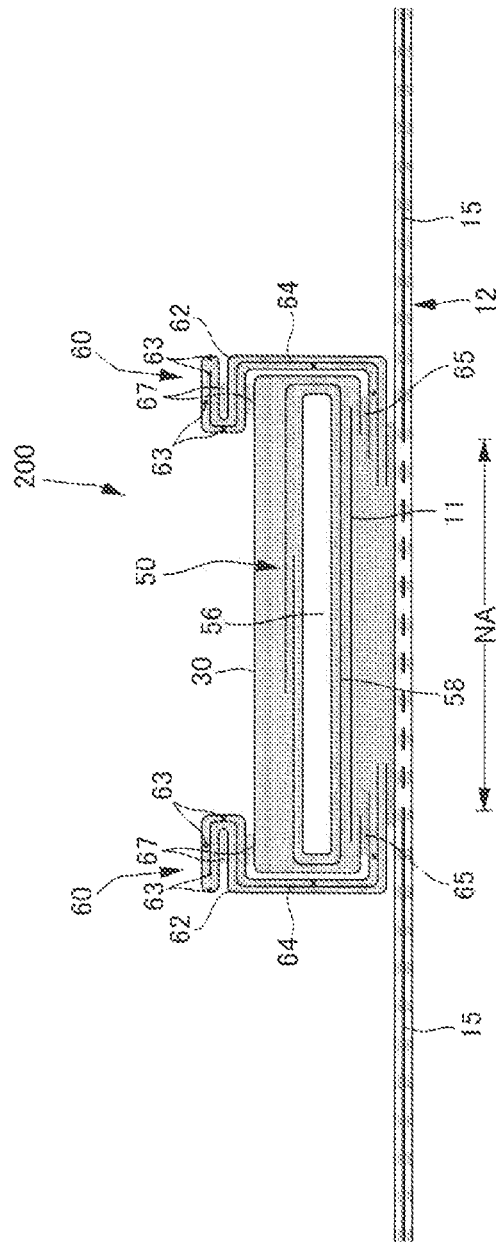
FIG. 4 is a cross-sectional view of FIG. 1 taken along line 4-4.
Figure 5:
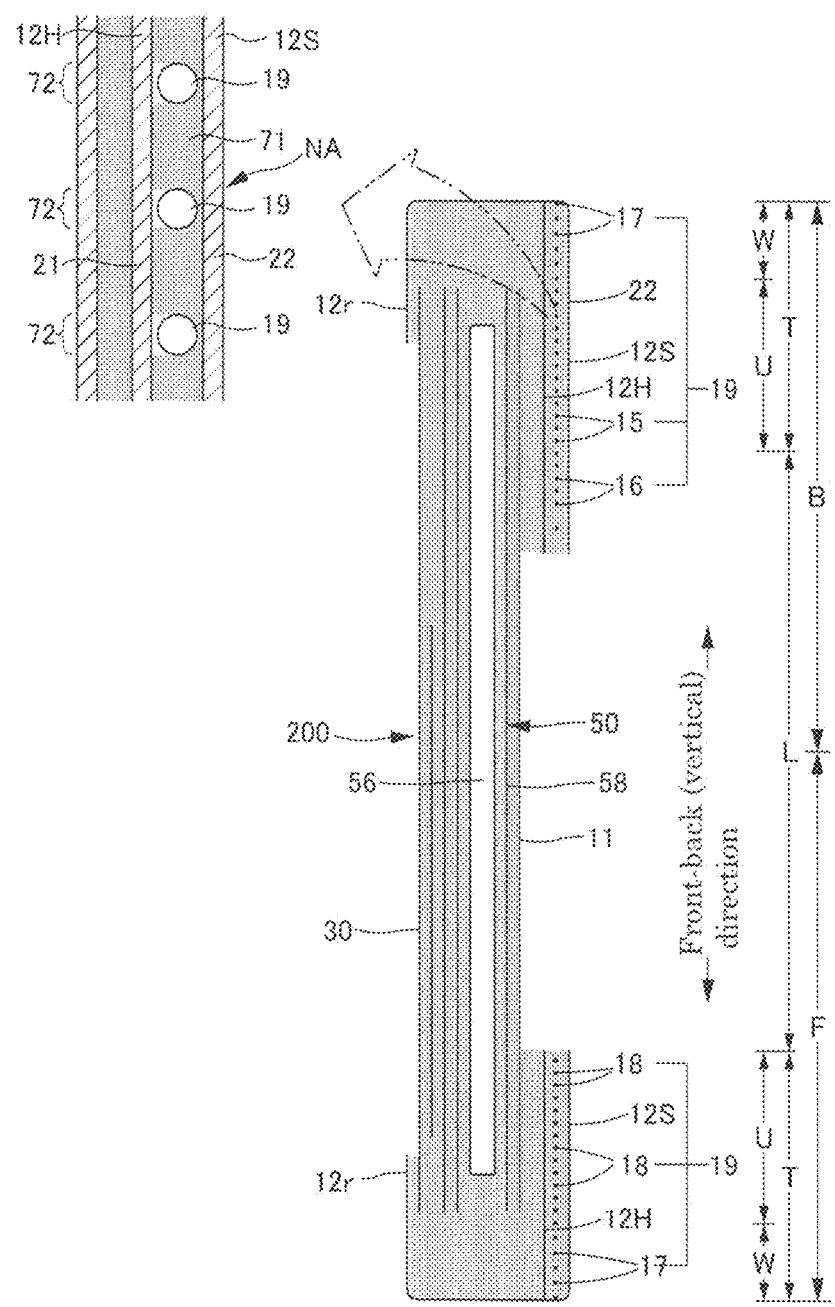
FIG. 5 is a cross-sectional view of FIG. 1 taken along line 5-5.

The inner body 200 may be formed in any shape, although it is rectangular in the illustrated form. The inner body 200 is a main body part with absorptive function that includes a top sheet 30 on the wearer's body side, a liquid impervious sheet 11, and an absorbent element 50 intervening between these sheets, as illustrated in FIGS. 3 to 5. Reference sign 40 indicates an interlayer sheet (second sheet) provided between the top sheet 30 and the absorbent element 50 to move quickly the liquid having passed through the top sheet 30 to the absorbent element 50 and to prevent reflowing. Reference sign 60 indicates three-dimensional gathers 60 standing from the both sides of the inner body 200 toward the wearer's body to prevent excretion from leaking toward the both sides of the inner body 200.

(Top Sheet)

The top sheet 30 is pervious to liquid and may be a porous or non-porous non-woven fabric or a porous plastic sheet, for example. There is no specific limitation on raw fibers for the non-woven fabric. For example, the raw fibers may be synthetic fibers based on olefin such as polyethylene and polypropylene, polyester, or polyamide, reproduced fibers of rayon, cupra, or the like, natural fibers of cotton or the like, and mixed fibers or composite fibers of two or more of the foregoing fibers. The non-woven fabric may be produced by any processing method. The processing method may be any of publicly known methods such as spun-lacing, spun-bonding, thermal bonding, melt-blowing, needle-punching, air-through processing, and point-bonding, for example. For flexibility and drape properties, spun-bonding and spun-lacing are preferred for example. For bulkiness and softness, air-through processing, point-bonding, and thermal bonding are preferred.

The top sheet 30 may be composed of a single sheet or a layered sheet obtained by sticking two or more sheets to each other. Similarly, the top sheet 30 may be composed of a single sheet or two or more sheets in a planar direction.

In the case of providing the three-dimensional gathers 60, it is preferred that both sides of the top sheet 30 are extended up to the back side of the absorbent element 50 through between the liquid impervious sheet 11 and the three-dimensional gathers 60, and are adhered to the liquid impervious sheet 11 and the three-dimensional gathers 60 by a hot-melt adhesive or the like to prevent liquid penetration.

(Interlayer Sheet)

To move the liquid having passed through the top sheet 30 quickly to the absorber, the interlayer sheet (also called as "second sheet") 40 higher in liquid permeation speed than the top sheet 30 may be provided. The interlayer sheet 40 can not only move the liquid quickly to the absorber with enhancement in absorption performance of the absorber but also prevent a "reflowing" phenomenon of the absorbed liquid from the absorber to keep the top sheet 30 in a dry state at any time. The interlayer sheet 40 may not be provided.

The interlayer sheet 40 may be made from the same material as that for the top sheet 30, or spun-laced, spun-bonded, SMS, or pulp non-woven fabric, or mixture sheet of pulp and rayon, point-bonded or crape paper, for example. In particular, air-through non-woven fabric is preferred due to its bulkiness. The air-through non-woven fabric preferably uses composite fibers of core-sheath structure. The resin for the core is acceptably polypropylene (PP) but preferably polyester (PET) with high rigidity. The basis weight of the fiber is preferably 20 to 80 g/m$^2$, more preferably 25 to 60 g/m$^2$. The fineness of raw fibers for the non-woven fabric is preferably 2.2 to 10 dtex. To increase the bulk of the non-woven fabric, all or some composite fibers of the raw fibers are preferably eccentric fibers with cores not centered, hollow fibers, or eccentric and hollow fibers.

The interlayer sheet 40 in the illustrated form is centered on an absorber 56 and is narrower than the absorber 56 in the width direction. Alternatively, the interlayer sheet 40 may be provided over the entire width of the absorber 56. The interlayer sheet 40 may be the same in length as the absorber 56, or may be shorter than the absorber 56, falling within the central area for receiving liquid.

(Liquid Impervious Sheet)

There is no particular limitation on the material for the liquid impervious sheet 11. For example, the liquid impervious sheet 11 may be a plastic film made from an olefin resin such as polyethylene and polypropylene, a laminate non-woven fabric with a plastic film on the surface of non-woven fabric, a layered sheet in which non-woven fabric and the like is laid on a plastic film. The liquid impervious sheet 11 is preferably made from a liquid-impervious and moisture-pervious material that has been favorably used in recent years for the viewpoint of prevention of stuffiness. As a widely used moisture-pervious plastic film, there is a microporous plastic film that is obtained by melting and kneading an inorganic filler in an olefin resin such as polyethylene and polypropylene to form a sheet and then elongating the sheet in a uniaxial or biaxial direction.

Besides, the liquid impervious sheet 11 may be a non-woven fabric of microdenier fibers, or may be a liquid impervious sheet that is formed without the use of a plastic film, by enhancing leak-proof performance by reducing the size of gaps between fibers with the application of heat or pressure or by coating the sheet with a high-water absorption resin, a hydrophobic resin, or a water repellent agent.

For enhancement of leak-proof performance, the liquid impervious sheet 11 is preferably extended through the both sides of the absorbent element 50 to the both sides of the absorbent element 50 at the top sheet 30 side. The appropriate width of the extended portion is about 5 to 20 mm at each of the right and left sides.

An excretion indicator changing in color by absorption of liquid may be provided at the inside of the liquid impervious sheet 11, in particular, on the side surface of the absorber 56.

(Three-Dimensional Gathers)

The three-dimensional gathers 60 are belt-like members extended entirely along the both sides of the inner body 200 in the front-back direction. The three-dimensional gathers 60 are provided to shut off urine or loose stool moving laterally over the top sheet 30 to prevent lateral leakage of the liquid. In this embodiment, the three-dimensional gathers 60 stand on the sides of the inner body 200. Each of the three-dimensional gathers 60 stands obliquely toward the central portion in the width direction at the base portion, and stands obliquely toward the outside in the width direction from the intermediate portion to the forward edge.

More specifically, each of the three-dimensional gathers 60 is formed such that a belt-like gather sheet 62 having the same length as the length of the inner body 200 in the front-back direction is folded back in two in the width direction, and a plurality of elongated resilient and elastic members 63 is fixed in the extended state along the longitudinal direction with spacing therebetween in the width direction between the sheets at a folded portion and its neighborhood. The base portions (ends opposite to the sheet folded portion in the width direction) of the three-dimensional gathers 60 positioned opposite to the forward edge portions constitute attachment portions 65 fixed to the under side surface of the inner body 200 at side edges. The portions of the three-dimensional gathers 60 other than the attachment portions 65 constitute protrusions 66 (folded portions) that protrude from the attachment portions 65. In addition, the protrusions 66 include the base portions toward the central side in the width direction and the edge portions that are folded back from the edges of the base portions toward the outside in the width direction. Although this form uses the three-dimensional gathers of surface-touching type, three-dimensional gathers (not illustrated) of a line-touching type that are not folded back toward the outside in the width direction may also be used. Then, while the both ends of the protrusions 66 in the front-back direction are front-back fixed portions 67 which are fixed to the side surfaces of the top sheet 30 in a lying down state with a hot-melt adhesive or a heat seal, the intermediate portions positioned therebetween are unfixed free portions to which the elongated resilient and elastic members 63 are fixed in the extended state along the front-back direction.

The gather sheet 62 may be preferably formed by applying a water repellent treatment with silicone or the like as necessary to flexible non-woven fabric excellent in uniformity and concealing performance such as spun-bonded non-woven fabric (SS, SSS, or the like), SMS non-woven fabric (SMS, SSMMS, or the like), and melt-blown non-woven fabric. The basis weight of the fibers is preferably about 10 to 30 g/m$^2$. The elongated resilient and elastic members 63 may be rubber threads or the like. In the case of using spandex rubber threads, the fineness of the threads is preferably 470 to 1240 dtex, more preferably 620 to 940 dtex. The extension ratio of the threads at the time of fixing is preferably 150 to 350%, more preferably 200 to 300%. In addition, a water-proof film 64 may intervene in the gather sheet folded in two as illustrated in the drawing.

The number of elongated resilient and elastic members 63 provided in the free portions of the three-dimensional gathers 60 is preferably two to six, more specifically three to five. The arrangement spacing 60$d$ is appropriately 3 to 10 mm. According to this configuration, the diaper is likely to touch the skin by surface with arrangement of the elongated resilient and elastic members 63. The elongated resilient and elastic members 63 may be arranged not only at the edge portions but also at the base portions.

The attachment portions 65 of the three-dimensional gathers 60 may be fixed to appropriate members in the inner body 200 such as the top sheet 30, the liquid impervious sheet 11, and the absorbent element 50.

In the thus configured three-dimensional gathers 60, the contraction force of the elongated resilient and elastic members 63 acts to make the both end portions in the front-back direction closer to each other. The both end portions of the protrusions 66 in the front-back direction are fixed so as not to stand, whereas the middle portions between the both ends of the protrusions 66 are non-fixed free portions. Accordingly, only the free portions stand to touch the wearer's body as illustrated in FIG. 3. In particular, when the attachment portions 65 are positioned on the back surface of the inner body 200, the three-dimensional gathers 60 stand and open outward in the width direction at the crotch portion and its neighborhood. Accordingly, the three-dimensional gathers 60 are brought into surface contact around the legs to produce an improved fit.

Figure 6:
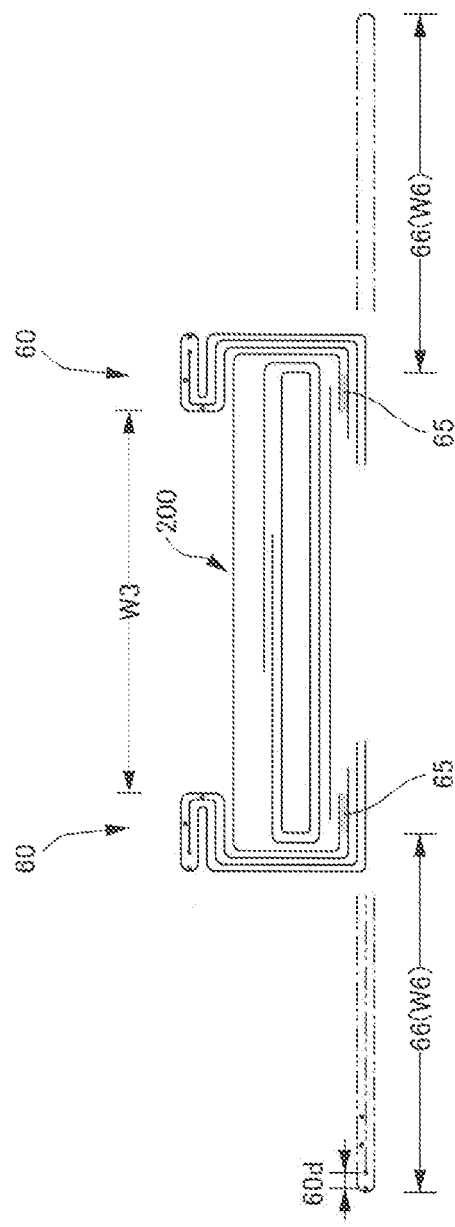
FIG. 6 is a cross-sectional view of only major components of the underpants-type disposable diaper.
Figure 7A:
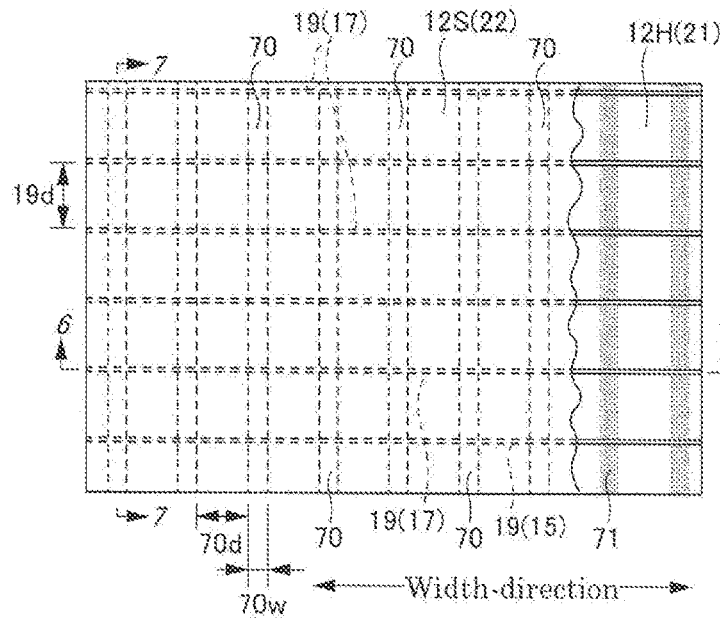
FIG. 7(a) is a planar view of a stretchable structure in the open state.
Figure 7D:
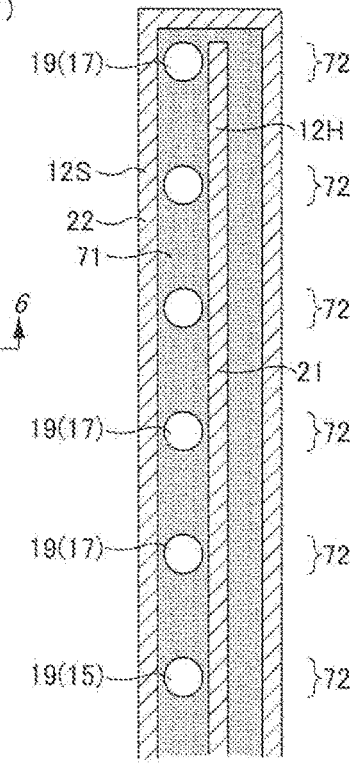
FIG. 7(d) is a cross-sectional view of the stretchable structure taken along line 7-7.
Figure 7B:
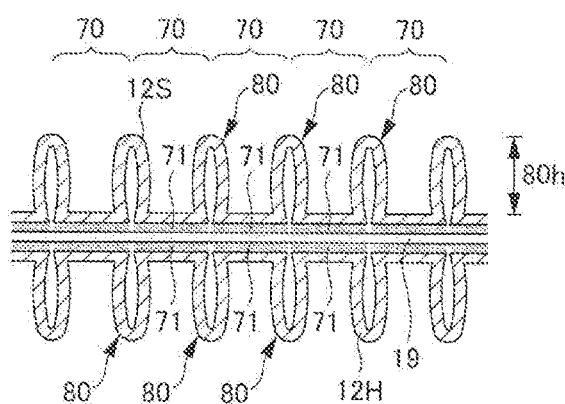
FIG. 7(b) is a cross-sectional view of the stretchable structure taken along line 6-6 in the state of natural length.
Figure 7C:
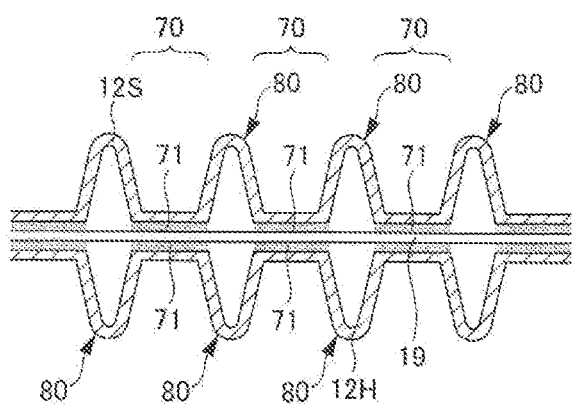
FIG. 7(c) is a cross-sectional view of the stretchable structure taken along line 6-6 in an extended state to some extent.

The dimensions of the three-dimensional gathers 60 can be decided as appropriate. In the case of a disposable diaper for infants, however, the standing height W6 (width of the protrusions 66 in an open state) is preferably 15 to 60 mm, more specifically 20 to 40 mm as illustrated in FIG. 6, for example. In addition, the separation distance W3 between the folds at the innermost side is preferably 60 to 190 mm, more preferably 70 to 140 mm in the flatly folded state where the three-dimensional gathers 60 are made parallel to the surface of the top sheet 30.

Unlike the illustrated form, the three-dimensional gathers may be provided doubly (in two rows) at each of the right and left sides of the inner body 200.

(Absorbent Element)

The absorbent element 50 has the absorber 56 and a wrapping sheet 58 for wrapping the entire absorber 56. The wrapping sheet 58 may not be provided.

(Absorber)

The absorber 56 may be formed from a fiber assembly. The fiber assembly may be fluff pulp fibers or accumulated short fibers such as synthetic fibers, or a filament assembly obtained by opening tows (fiber bundles) of synthetic fibers such as cellulose acetate, as necessary. The basis weight of fluff pulp or accumulated short fibers may be about 100 to 300 g/m$^2$, and the basis weight of a filament assembly may be about 30 to 120 g/m$^2$, for example. The fineness of synthetic fibers is, for example, 1 to 16 dtex, preferably 1 to 10 dtex, more preferably 1 to 5 dtex. In the case of a filament assembly, the filaments may be non-crimped fibers but are preferably crimped fibers. The number of crimps in the crimped fibers may be, for example, about 5 to 75 per inch, preferably about 10 to 50 per inch, more preferably about 15 to 50 per inch. The crimped fibers are evenly crimped in many cases. High-absorbent polymer particles are preferably dispersed and held in the absorber 56.

The absorber 56 may be rectangular in shape but preferably has an hourglass shape having a front end portion, a back end portion, and a narrower portion that is positioned between the front and back end portions and is narrower than the two end portions as illustrated in FIG. 1 to improve the absorber 56 and the three-dimensional gathers 60 in a fit of the edges around the legs.

The dimensions of the absorber 56 can be decided as appropriate. Nevertheless, the absorber preferably extends to the peripheral edges or their neighborhoods of the inner body in the front-back direction and the width direction. Reference sign 56X indicates the width of the absorber 56.

(High-Absorbent Polymer Particles)

The absorber 56 may partially or entirely contain high-absorbent polymer particles. The high-absorbent polymer particles include "powders" as well as "particles". The diameter of the high-absorbent polymer particles 54 may be the same as that of particles for general use in this type of absorbent article. For example, the ratio of particles that remain on a sieve after sieving (shaking for five minutes) with a standard sieve (JIS Z8801-1:2006) of 500 μm is preferably 30 weight % or less. Alternatively, the ratio of particles that remain on the sieve after sieving (shaking for five minutes) with the standard sieve (JIS Z8801-1:2006) of 180 μm is preferably 60 weight % or more.

There is no particular limitation on the material for the high-absorbent polymer particles but the material preferably has a water absorption capacity (JIS K7223-1996 "Testing method for water absorption capacity of super absorbent polymers") of 40 g/g or more. The high-absorbent polymer particles may be based on starch, cellulose, or synthetic polymer. The high-absorbent polymer particles may be made of a starch-acrylic acid (salt) graft copolymer, a saponified material of starch-acrylonitrile copolymer, a crosslinking substance of carboxymethyl-cellulose sodium, an acrylic acid (salt) polymer, or the like. The high-absorbent polymer particles are preferably used in a general particulate form but may be used in another form.

The water absorption rate (JIS K7224-1996 Testing method for water absorption rate of super absorbent polymers) of the high-absorbent polymer particles is preferably 40 seconds or less. At a water absorption rate of more than 40 seconds, the absorbed liquid is more likely to flow back from the absorber 56 to the outside of the absorber 56 (so called "reflowing").

The basis weight of the high absorbent polymer particles can be decided as appropriate depending on the absorption volume required in the use of the absorber 56. Therefore, although being not specified absolutely, the basis weight may be 50 to 350 g/m$^2$. When the basis weight of the polymer is lower than 50 g/m$^2$, it is hard to assure the absorption volume. When the basis weight of the polymer exceeds 350 g/m$^2$, the effect becomes saturated.

If necessary, the high-absorbent polymer particles can be adjusted in dispersing density or dispersing quantity along the planar direction of the absorber 56. For example, the dispersing quantity of the high-absorbent polymer particles may be larger in the excretion region than the other regions. With regard to gender differences, the dispersing density (quantity) of the high-absorbent polymer particles may be increased at the front side of the product for male, and may be increased at the central part of the product for female. In addition, the polymer may not be provided locally (in spots for example) in the absorber 56 in the planar direction.

(Wrapping Sheet)

In the case of using the wrapping sheet 58, the material thereof may be tissue paper, in particular, crape paper, non-woven fabric, polyethylene-laminated non-woven fabric, a porous sheet, or the like. However, the material sheet is desirably configured to retain the high-absorbent polymer particles. In the case of using non-woven fabric instead of crape paper, the hydrophilic SMS non-woven fabric (SMS, SSMMS, or the like) is preferred in particular and its material may be polypropylene, polyethylene/polypropylene composite, or the like. The basis weight of the material is desirably 5 to 40 g/m$^2$, in particular 10 to 30 g/m$^2$.

The form of wrapping by the wrapping sheet 58 can be decided as appropriate. Nevertheless, from the viewpoint of ease of producing and prevention of leakage of the high-absorbent polymer particles from the front and back end edges, the wrapping sheet 58 preferably wraps the absorber 56 in a cylindrical form to surround the front and back surfaces and both side surfaces of the absorber 56, and has front and back edges extended off from the upper side surface and under side surface of the absorber 56 so that the extended portions are crushed in the upper side-under side direction and joined together by a joint means such as a hot-melt adhesive.

(Crotch Portion Cover Sheet)

To the back surface of the liquid impervious sheet in the inner body, a crotch portion cover sheet can be attached so as to cover a part of exposed portion of the inner body (for example, along the entire front-back direction of the exposed portion between the ventral side outer body and the dorsal side outer body but not extending to the front and back ends of the inner body, or both side edges in the width direction not reaching the both side edges of the inner body) or the entire inner body. A material for the crotch portion cover sheet similar to that of the outer bodies and may be used as explained below.

(Outer Body)

The outer bodies 12F and 12B have waist portions T having the side seal portions 12A and determined as vertical areas (vertical areas from the waist opening WO to the upper ends of the leg openings LO) and an intermediate portion L determined as a front-back area of a portion forming the leg openings LO (between a vertical region of the ventral side outer body 12F having the side seal portions 12A and a vertical region of the dorsal side outer body 12B having the side seal portions 12A). The waist portions T are conceptually divided into "waist edge portions" W forming the edge of the waist opening and "lower waist portions" U as the portions under the waist edge portions W. Normally, when there are boundaries at which stretching stress (for example, the thickness or the extension ratio of resilient and elastic members) in the width direction changes in the waist portions T, portions closer to the waist opening WO relative to boundaries closest to the waist opening WO correspond to the waist edge portions W. When there are no boundaries like this, portions closer to the waist opening WO relative to the absorber 56 or the inner body 200 correspond to the waist edge portions W. The lengths of these portions in the vertical direction vary depending on the size of the product and can be decided as appropriate. As an example, the length of the waist edge portion W may be 15 to 40 mm, and the length of the lower waist portion U may be 65 to 120 mm. On the other hand, the intermediate portion L can be also omitted or the intermediate portions L can be provided on both of the ventral side outer body and the dorsal side outer body. In the form illustrated in the drawings, the intermediate portion L is provided on only the dorsal side outer body 12B and covers buttocks. When the edges of the intermediate portion L at the leg sides are formed into curved shapes so as to be along the circumferences of the legs, the fit to the circumferences of the legs are excellent and it is therefore preferable.

The outer bodies 12F and 12B are constituted by the ventral side outer body 12F and the dorsal side outer body 12B, and the ventral side outer body 12F and the dorsal side outer body 12B are not continuous at the leg sides and are separated from each other. A separation distance L8 therebetween may be set to approximately 150 to 250 mm. A part or the entire of the region of the inner body 200, which is exposed between the ventral side outer body 12F and the dorsal side outer body 12B, can be also covered by the cover sheet (not illustrated). As a material of the cover sheet in this case, that same as the material forming the outer bodies 12F and 12B can be used. On the other hand, as in an example illustrated in FIG. 9 to FIG. 12, the front panel F to the back panel B can be also configured to be covered continuously by an integral outer body 12.

Each of the ventral side outer body 12F and the dorsal side outer body 12B is formed by joining two sheet materials 12S and 12H together as illustrated in FIG. 5 and FIG. 7. The first sheet materials 12S located at the outer side are folded back inside at the edges of the second sheet materials 12H at the waist opening WO side. Folded portions 12r extend so as to cover the end portions of the inner body 200 at the waist side.

There is no specific limitation on the sheet materials 12S and 12H as far as they are sheets, but they are preferably formed from non-woven fabric. There is no specific limitation on raw fibers for the non-woven fabric. For example, the raw fibers may be synthetic fibers based on olefin such as polyethylene and polypropylene, polyester, or polyamide, reproduced fibers of rayon or cupra, natural fibers of cotton or the like, or mixed fibers or composite fibers of two or more of the foregoing fibers. The non-woven fabric may be produced by any processing method. When importance is placed on the flexibility, non-woven fabric (hereinafter, also referred to as PP-based non-woven fabric) formed with polypropylene (PP) or a copolymer thereof (for example, copolymer obtained by blending polyethylene or ethylene as a copolymerization component) or non-woven fabric formed with core-sheath fibers (PE/PP) composed of polyethylene (PE) as a sheath component and polypropylene (PP) as a core component is preferably used as at least one of the first sheet material 12S and the second sheet material 12H. The processing method may be any of publicly known methods such as spun-lacing, spun-bonding, thermal bonding, melt-blowing, needle-punching, air-through processing, and point-bonding, for example. In particular, spun-bonded non-woven fabric is preferable because the strength and flexibility are excellent and spun-bonded non-woven fabric formed by laminating a plurality of spun-bonded layers, for example, SS non-woven fabric (two layers) or SSS non-woven fabric (three layers) can be used preferably. Spun-bonded non-woven fabric formed by laminating equal to or more than four spun-bonded layers can be also used. Although the thickness and the basis weight of the non-woven fabric are not particularly limited, it is desired that the thickness thereof is approximately 0.1 to 1 mm and the basis weight thereof is approximately 10 to 20 g/m$^2$. Each of the sheet materials 12S and 12H may be composed of a single non-woven fabric sheet or any one or both of them may be composed of a layered non-woven fabric sheet obtained by stacking a plurality of non-woven fabric sheets to one another.

In the ventral side outer body 12F and the dorsal side outer body 12B, the elongated resilient and elastic members 19 (waist edge portion resilient and elastic members 17, lower waist portion resilient and elastic members 15, and intermediate portion resilient and elastic members 16, which will be described later) such as the rubber threads are provided between the inside layers 21 and the outside layers 22 formed by at least one of both the sheet materials 12S and 12H at a predetermined extension ratio to enhance the fit to the wearer's waist and the like. The elongated resilient and elastic members 19 may be formed from synthetic rubber or natural rubber.

Figure 10:
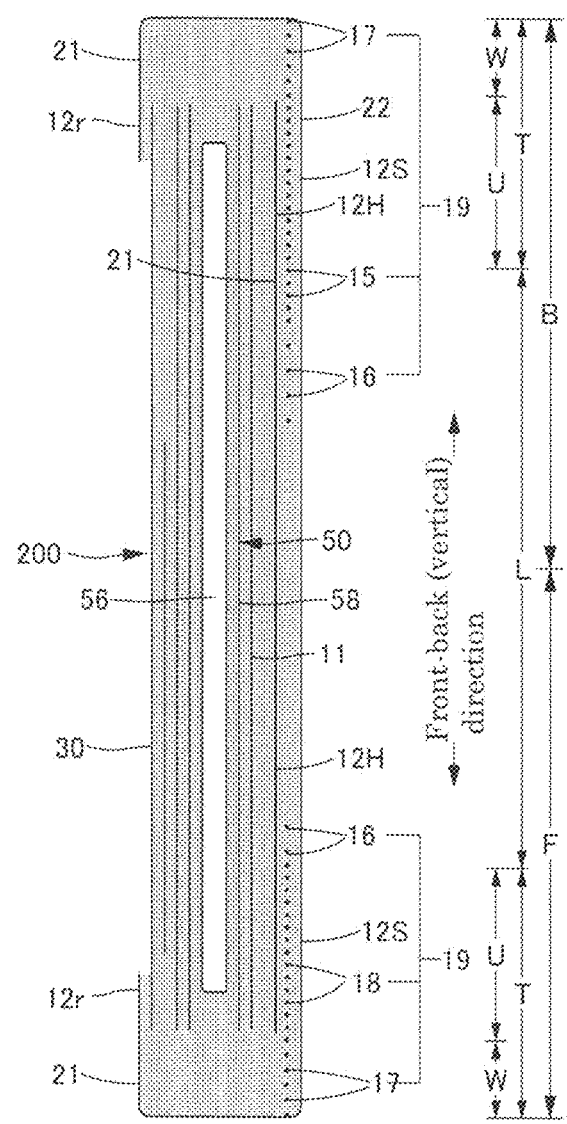
FIG. 10 is a cross-sectional view of FIG. 9 taken along line 5-5.
Figure 11:
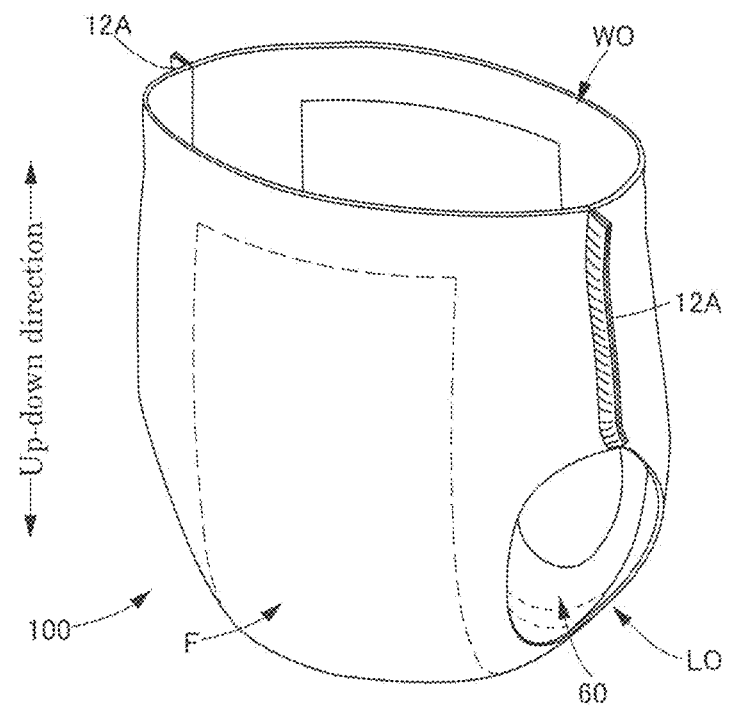
FIG. 11 is a perspective view of the underpants-type disposable diaper.
Figure 12:
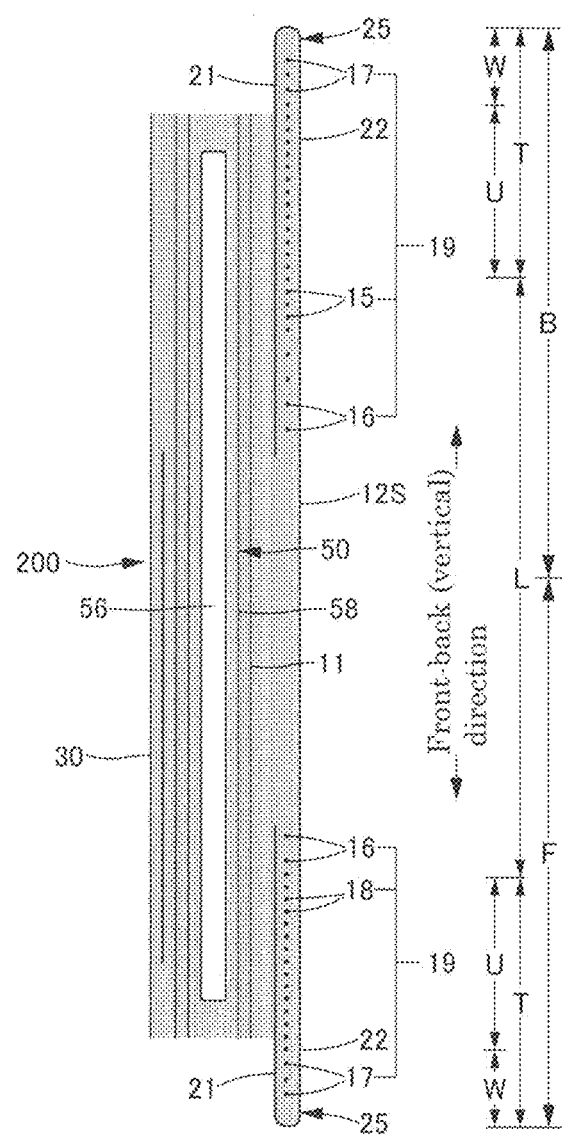
FIG. 12 is a vertical cross-sectional view of the underpants-type disposable diaper.

Although in the form illustrated in FIG. 5, the outside layers 22 facing the outer side of the resilient and elastic members 19 are formed by the first sheet materials 12S and the inside layers 21 facing the inner side of the resilient and elastic members 19 are formed by the second sheet materials 12H, any of publicly known structures of the inside layers 21 and the outside layers 22 can be used with no specific limitation. For example, the inside layer 21 and the outside layer 22 can be formed as follows. That is, as illustrated in FIG. 10, the inside layer 21 is formed by the folded portions 12r of the first sheet material 12S and the outside layer 22 is formed by the outer side portion of the first sheet material 12S in the waist edge portions W, and the inside layer 21 is formed by the second sheet material 12H and the outside layer 22 is formed by the outer side portion of the first sheet material 12S in the lower waist portions U and the intermediate portion L. As illustrated in FIG. 12, the inside layer 21 and the outside layer 22 can be also configured by folding back the first sheet material 12S inside (the first sheet material 12S can be folded back outside) at the edges of the waist opening. The example illustrated in FIG. 12 employs the form in which the front panel F and the back panel B are continuously covered by the integral outer body 12. However, also in the form in which the outer body 12 is divided into the ventral side outer body 12F and the dorsal side outer body 12B, as illustrated in various forms in FIG. 8, the inside layer 21 and the outside layer 22 can be formed as follows. That is, in at least one of the ventral side outer body 12F and the dorsal side outer body 12B, all of the inside layer 21 and the outside layer 22 are formed by folding back one sheet material or parts of the inside layer 21 and the outside layer 22 are formed by folding back one sheet material whereas the remaining parts of the inside layer 21 and the outside layer 22 are formed by bonding two sheet materials to each other. It should be noted that a reference numeral 12d indicates a separation portion of the sheet materials adjacent to each other in the vertical direction and a reference numeral 12w indicates an overlapped portion of the sheet materials. Furthermore, as in a form illustrated in FIG. 23 and FIG. 24, in the ventral side outer body 12F and the dorsal side outer body 12B (or any one of them), all of the inside layers 21 and the outside layers 22 are formed by folding back one sheet material at the crotch side and the waist side.

Although in the form illustrated in FIG. 5 and the like, the folded portions 12r to the inner side relative to the inside layers 21 are formed, as illustrated in FIG. 12 and FIG. 8, the folded portions 12r to the inner side relative to the inside layers 21 can be also omitted.

The elongated resilient and elastic members 19 may be made from a synthetic rubber or a natural rubber. The elongated resilient and elastic members 19 can be uniformly provided over the entire outer body, it is preferable, however, to make fineness, spacing, or the like different depending on a position of the outer bodies 12F and 12B. Thus, in the illustrated form, a plurality of waist edge resilient and elastic members 17 is fixed at the waist edge portion W in the extended state along the width direction at a predetermined extension ratio with spacing therebetween in the up-down direction in such a manner as to be entirely continuous in the width direction. One or more of the waist edge resilient and elastic members 17 in a region adjacent to the lower waist portion U may overlap the inner body 200 or may be provided on, except for a central portion in the width direction overlapping with the inner body 200, both lateral sides of the central portion so as to be continuous in the width direction. As the waist edge resilient and elastic members 17, about 3 to 22 rubber threads with a fineness of 155 to 1880 dtex, in particular about 470 to 1240 dtex (This is applied in the case of a synthetic rubber. In the case of a natural rubber, a cross-section area of 0.05 to 1.5 $mm^2$, in particular about 0.1 to 1.0 $mm^2$) are preferably fixed at an extension ratio of 150 to 400%, in particular about 220 to 320%, with spacing of 4 to 12 mm. All of the waist edge resilient and elastic members 17 may not be equal in thickness and extension ratio. For example, the resilient and elastic members may be different in fineness and extension ratio between the upper and lower sides of the waist edge portions W.

In the lower waist portions U, the plurality of lower waist portion resilient and elastic members 15 and 18 formed by the elongated resilient and elastic members are fixed with a predetermined extension ratio in an extended state along the width direction so as to be spaced from each other in the up-down direction such that the middle or entire areas of the regions for fixing the inner body 200 in the width direction are non-stretchable regions NA and stretchable regions are formed over the entire regions between the non-stretchable regions NA and the side seal portions 12A in the width direction.

As the lower waist portion resilient and elastic members 15 and 18, about 5 to 30 rubber threads with a fineness of 155 to 1880 dtex, in particular about 470 to 1240 dtex (This is applied in the case of a synthetic rubber. In the case of a natural rubber, a cross-section area of 0.05 to 1.5 $mm^2$, in particular about 0.1 to 1.0 $mm^2$) are preferably fixed at an extension ratio of 200 to 350%, in particular about 240 to 300%, with spacing of 1 to 15 mm, in particular 3 to 8 mm.

Figure 9:
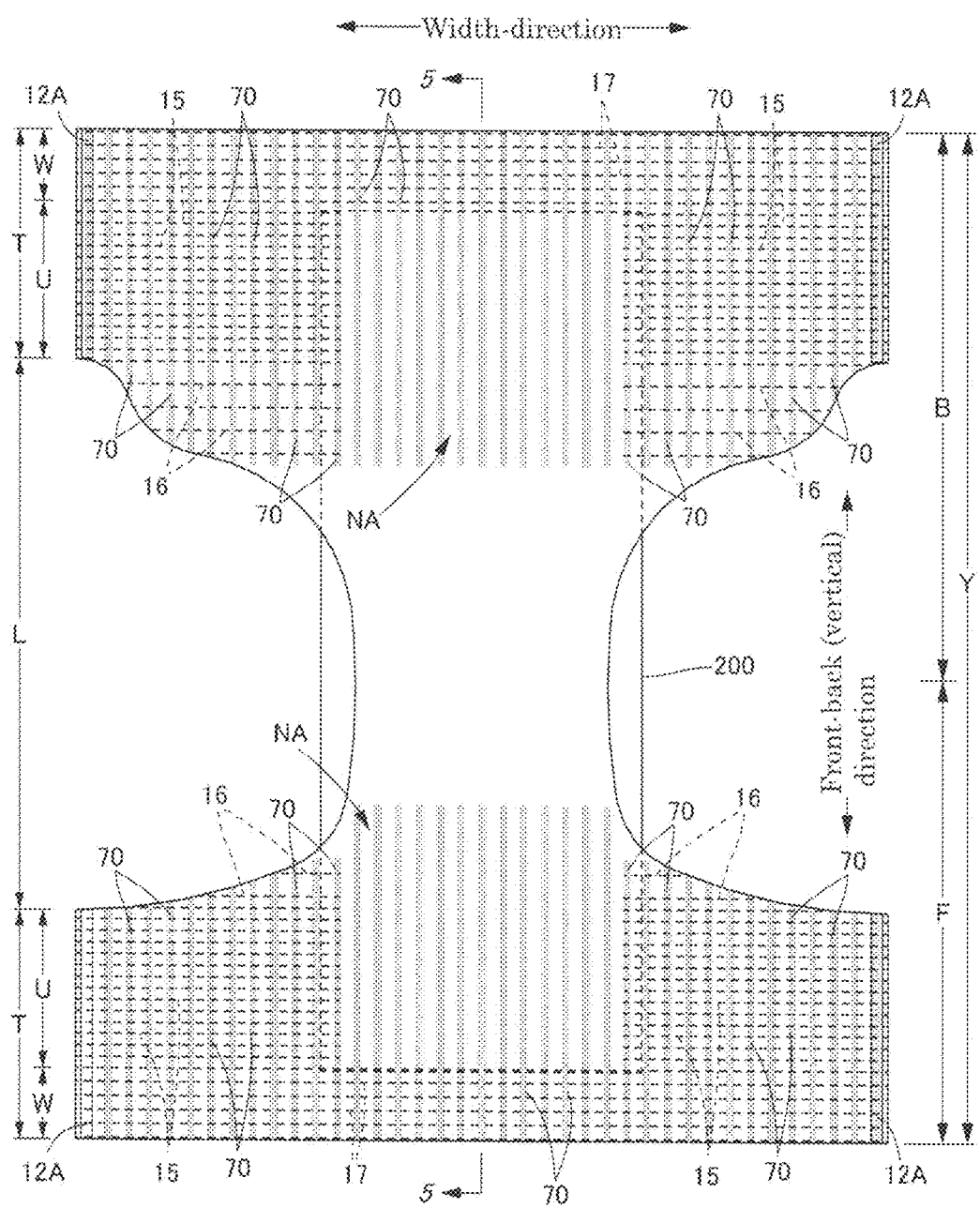
FIG. 9 is a planar view of the internal surface of the underpants-type disposable diaper in the open state.

In the intermediate portion L, the plurality of intermediate portion resilient and elastic members 16 are fixed with a predetermined extension ratio in an extended state along the width direction so as to be spaced from each other in the up-down direction such that the middle or entire area of the region for fixing the inner body 200 in the width direction is the non-stretchable region NA and the stretchable regions are formed over the entire regions between the non-stretchable region NA and the side seal portions 12A in the width direction. Although in the form illustrated in FIG. 2 and the like, the intermediate portion L is provided at only the dorsal side, in addition thereto (or instead thereof (not illustrated)), the intermediate portion L can be also provided at the ventral side as illustrated in FIG. 9 and the like.

As the intermediate resilient ad elastic members 16, about 2 to 10 rubber threads with a fineness of 155 to 1880 dtex, in particular about 470 to 1240 dtex (This is applied in the case of a synthetic rubber. In the case of a natural rubber, a cross-section area of 0.05 to 1.5 $mm^2$, in particular about 0.1 to 1.0 $mm^2$) are preferably fixed at an extension ratio of 150 to 300%, in particular about 180 to 260%, with spacing of 5 to 40 mm, in particular 5 to 20 mm.

When the middle or entire areas of the regions for fixing the inner body 200 in the width direction are the non-stretchable regions NA and the stretchable regions are formed over the entire regions between the non-stretchable regions NA and the side seal portions 12A in the width direction as illustrated in the drawings, the inner body 200 is not deformed in a contraction manner in the width direction with the contraction force of the resilient and elastic members 19 and deterioration in absorbing performance or appearance can be prevented. The foregoing form includes the form in which no resilient and elastic member 19 resides in the non-stretchable regions NA and the form in which the resilient and elastic members 19 also reside in the non-stretchable regions NA but the resilient and elastic members 19 are finely cut in the width direction and exert no contraction force in the non-stretchable regions NA (this is substantially equal to the case in which no resilient and elastic member 19 is provided). As a matter of course, the arrangement forms of the lower waist portion resilient and elastic members 15 and 18 and the intermediate portion resilient and elastic members 16 are not limited to the foregoing ones. Alternatively, some or all of the lower waist portion resilient and elastic members 15 and 18 and the intermediate portion resilient and elastic members 16 may be provided crossing over the inner body 200 between both the side seal portions 12A and the entire stretchable regions in the width direction can be also provided.

As characteristic properties, as illustrated in FIG. 7, the entire stretchable regions (or a part of the stretchable regions) formed in the ventral side outer body 12F and the dorsal side outer body 12B have the sheet joined sections 70 in which the inside layers 21 and the outside layers 22 are joined together with an adhesive 71 applied in the vertical striped pattern intermittent in the width direction and the resilient and elastic members 19 are fixed to the inside layers 21 and the outside layers 22 with the adhesive 71 continuous in the vertical direction at both the inner and outer sides of the resilient and elastic members 19 in portions in which the sheet joined sections 70 and the resilient and elastic members 19 intersect with each other. In the stretchable regions, the sheet joined sections 70 are formed into a vertical striped pattern with the adhesive 71 continuous in the vertical direction at both the inner and outer sides of the resilient and elastic members 19 and portions of the first sheet materials 12S and the second sheet materials 12H, which are located between the sheet joined sections 70, contract with contraction of the resilient and elastic members 19 and swell to the directions opposite to each other, thereby forming pleats 80, as illustrated in FIG. 7(b). Although FIG. 7(b) illustrates the state of the natural length, the resilient and elastic members 19 are made to extend to some extent from this state when attached. With this, routes of the ridges 80 spread and the heights 80h of the pleats 80 therefore become lower, as illustrated in FIG. 7(c). This stretchable structure is a vertical continuous joined form. Therefore, the pleats 80 formed in the stretchable regions vertically and straightly extend along the sheet joined sections 70 and appearance and air permeability are excellent. In addition, the resilient and elastic members 19 in the stretchable regions are made to firmly adhere to both the inside layers 21 and the outside layers 22 with the adhesive 71 continuous in the vertical direction at both the inner and outer sides of the resilient and elastic members 19 in the portions intersecting with the adhesive 71 on the sheet joined sections 70. Accordingly, the drawing preventing performance of the resilient and elastic members 19 is excellent.

Although not illustrated in the drawings, in order to make the drawing preventing performance more excellent, the following is also one preferable form. That is, the resilient and elastic members 19 in both the end portions of the stretchable regions in the width direction, which do not intersect with the sheet joined sections 70 with the adhesive 71 applied in the vertical striped pattern, are fixed to the inside layers 21 and the outside layers 22 with the adhesive 71 applied to the outer circumferential surfaces of the resilient and elastic members 19. It should be noted that the adhesive 71 can be applied to the outer circumferential surfaces of the resilient and elastic members 19 in portions other than both the end portions of the stretchable regions, for example, the non-stretchable regions NA if necessary. However, the adhesive 71 is not applied to the outer circumferential surfaces of the resilient and elastic members 19 in the area between both the end portions of the stretchable regions in the MD direction.

As illustrated in the drawings, in the form in which middle or entire areas of the regions for fixing the inner body 200 in the width direction are the non-stretchable regions NA formed by cutting the resilient and elastic members 19 and the stretchable regions are formed over the entire areas between the non-stretchable regions NA and the side seal portions 12A in the width direction, the fine pieces of the resilient and elastic members 19 after cut preferably contract without involving the inside layers 21 and the outside layers 22 in the non-stretchable regions NA and it is therefore sufficient that adhesion force of the resilient and elastic members 19 is weak. Accordingly, as illustrated in an enlarged manner in FIG. 5, in the non-stretchable regions NA, it is also preferable that the adhesive 71 be non-continuous vertically at any one side of the inner and outer sides of the resilient and elastic members 19 in the portions in which the sheet joined sections 70 and the resilient and elastic members 19 intersect with each other. With this, reduction in the usage amount of the adhesive 71 and improvement in flexibility of the outer body 12 in the non-stretchable regions NA can be improved.

The width 70w of each sheet joined section 70 and an interval 70d (see FIG. 7) between the adjacent sheet joined sections 70 can be decided as appropriate, but the dimension 70w of each sheet joined section 70 in the width direction is preferably 0.5 to 4 mm and the interval 70d between the adjacent sheet joined sections 70 is preferably 4 to 8 mm (in particular, 5 to 7 mm). From the viewpoint of ease of production, the lower limit of the dimension 70w of the sheet joined section 70 in the width direction is preferably set to 1 mm, but from the viewpoint of flexibility, the lower limit thereof is preferably set to 0.5 mm. On the other hand, the upper limit of the dimension 70w of the sheet joined section 70 in the width direction is preferably set to 2 mm, more preferably 1.5 mm.

The width 70w of each sheet joined section 70 influences the interval between the adjacent pleats 80. When the pleats 80 are formed thin as in the vertical continuous joined form, if the width exceeds 4 mm, the interval between the adjacent pleats 80 is excessively increased and the individual pleats 80 seem to be independent. In addition, in such a case, if the pleats 80 are deformed (for example, collapse, spread, or lie down) with compression force in the thickness direction, mutual support action of the adjacent pleats 80 is weakened. Consequently, resistance to the deformation or restoration after the deformation is also lowered, resulting in insufficient softness.

In addition, when the interval 70d between the adjacent sheet joined sections 70 is set to be less than 4 mm or more than 8 mm only by simply setting the width 70w of each sheet joined section 70 to 0.5 to 4 mm, the following result is provided. That is, the interval 70d between the adjacent sheet joined sections 70 influences the height 80h and the width of the pleats 80. When the interval 70d between the adjacent sheet joined sections 70 is approximately 2 mm, vertical continuity of the pleats 80 is poor as in the case of continuous fixing in the width direction (provision of the sheet joined sections 70 intermittently in the width direction makes no sense). When the interval 70d between the adjacent sheet joined sections 70 is 3 mm, the pleats 80 vertically and straightly extend, but the mutual support action of the adjacent pleats 80 cannot be expected, resulting in insufficient softness. When the interval 70d between the adjacent sheet joined sections 70 is more than 8 mm, the pleats 80 collapse irregularly due to compression at the time of packaging and appearance of the product is deteriorated. Only when the width 70w of each sheet joined section 70 is set to 0.5 to 4 mm and the interval 70d between the adjacent sheet joined sections 70 is set to 4 to 8 mm, sufficient softness is provided and the pleats 80 can be made difficult to collapse irregularly due to the compression at the time of packaging (in other words, pleats extending straightly, which have sufficient heights and are difficult to lie down, can be provided). Moreover, when the sheet joined sections 70 are formed by welding in the vertical continuous joined form, hard lines are undesirably formed and lowering in the flexibility cannot be avoided. However, when the sheet joined sections 70 are formed with the adhesive 71, lowering in the flexibility due to material welding does not occur and flexibility is more excellent.

The sheet joined sections 70 are intermittent in the width direction in the foregoing stretchable regions. Therefore, lowering in fixing force of the resilient and elastic members 19 cannot be avoided and there is a risk that the resilient and elastic members 19 are detached. In particular, although it is preferable that the width 70w of each sheet joined section 70 be small, in this case, the portions in which the resilient and elastic members 19 and the sheet joined sections 70 intersect with each other are small. This requires the resilient and elastic members 19 to be fixed in the small portions and ensuring of the fixing force of the resilient and elastic members 19 is therefore important. Accordingly, when the sheet joined sections each having the small width are provided as described above, the above-mentioned both-sided application is preferable.

The non-woven fabric is preferably used as the first sheet materials 12S and the second sheet materials 12H. However, in this case, when the bending resistance thereof in the width direction is lower, the pleats 80 are formed into thin acute shapes and are easy to lie down and the compression resilience thereof in the thickness direction is poor. In order to improve them, the basis weight of the non-woven fabric can be increased. This however raises a risk that stiff feeling is increased (stiffness is excessively increased) and the softness when touched is deteriorated even if softness in appearance is provided. For this reason, it is preferable that the non-woven fabric be used as the first sheet materials 12S and the second sheet materials 12H and the bending resistance thereof in the width direction be higher than the bending resistance in the vertical direction. With this, the pleats 80 are easy to swell roundly and the compression resilience in the thickness direction is increased. In addition, the pleats 80 are difficult to lie down and are rich in softness when touched. The bending resistance of each of the first sheet material 12S and the second sheet material 12H in the width direction is preferably 30 to 75 mm, more preferably 40 to 55 mm. The bending resistance of each of the first sheet material 12S and the second sheet material 12H in the vertical direction is preferably 20 to 50 mm, more preferably 25 to 35 mm within a range of lower than the bending resistance thereof in the width direction.

The bending resistance of the non-woven fabric refers to a value that is measured in accordance with a bending resistance A method (45-degree cantilever method) defined in JIS L1096:2010 "Testing methods for woven and knitted fabrics".

For setting the bending resistance of the non-woven fabric in the vertical direction to be lower than the bending resistance thereof in the width direction, it is sufficient that fiber orientation of the non-woven fabric is made along the width direction. The fiber orientation represents the direction along which fibers of the non-woven fabric are. What "the fiber orientation is along the width direction" encompasses the case in which the fibers corresponding to 100% of the total fiber weight forming the non-woven fabric are orientated to the width direction to the case in which the fibers corresponding to equal to or higher than 50% thereof are orientated in a range of $-45°$ to $+45°$ with respect to the width direction. A generally used measurement method can be used for a method for measuring the fiber orientation of the non-woven fabric. Examples of the measurement method include a measurement method based on a fiber orientation test with zero distance tensile strength in accordance with TAPPI standard T481, and a simple measurement method in which the fiber orientation direction is decided from a tensile strength ratio between the width direction and the direction orthogonal thereto. In the latter simple measurement method, a tensile test is performed using a test piece having the length of 200 mm and the width of 50 mm under a condition where a cross head speed is 500 mm/min and a distance between chucks is 150 mm with a tensile testing machine so as to calculate the tensile strength from the maximum load at the time of pulling. When the tensile strength ratio (width direction/vertical direction) is higher than 1, the fiber orientation is considered to be along the width direction.

An interval 19d (see FIG. 7) between the adjacent resilient and elastic members 19 can be decided as appropriate. However, when the interval 19d is larger than 10 mm, the thickness of the pleats 80 changes in the vertical direction although the change amount thereof is not as large as that in the vertical intermittent joined form, and the pleats 80 become fluffy. Therefore, the interval 19d between the adjacent resilient and elastic members 19 is preferably equal to or smaller than 10 mm, particularly preferably 3 to 7 mm.

It is sufficient that the fineness and the extension ratio (extension ratio in a state in which the stretchable structure is completely opened) of the resilient and elastic members 19 are selected as appropriate in accordance with attachment positions of the resilient and elastic members 19 and preferred ranges thereof are as described above. Generally, the fineness of the resilient and elastic members 19 is approximately 300 to 1,000 dtex and the extension ratio thereof is desirably approximately 200 to 350%.

(Others)

In the foregoing example, the same stretchable regions are formed not only in the waist edge portions W of the underpants-type disposable diaper but also in the area from the lower waist portions U to the intermediate portion L of the underpants-type disposable diaper. However, another publicly known stretchable structure may be applied to a part of the waist edge portions W, the lower waist portions U, and the intermediate portion L or the resilient and elastic members 16 may not be provided in the intermediate portion L. In addition, in the example as illustrated in the drawings, the sheet joined sections 70 in the respective panels are continuous in the vertical direction while including the waist edge portions W. Alternatively, the sheet joined sections 70 in the waist edge portions W and the sheet joined sections 70 in the lower waist portions U can be formed individually so as to be spaced from each other.

<Example of a Method of Producing an Underpants-Type Disposable Diaper>

Figure 13:
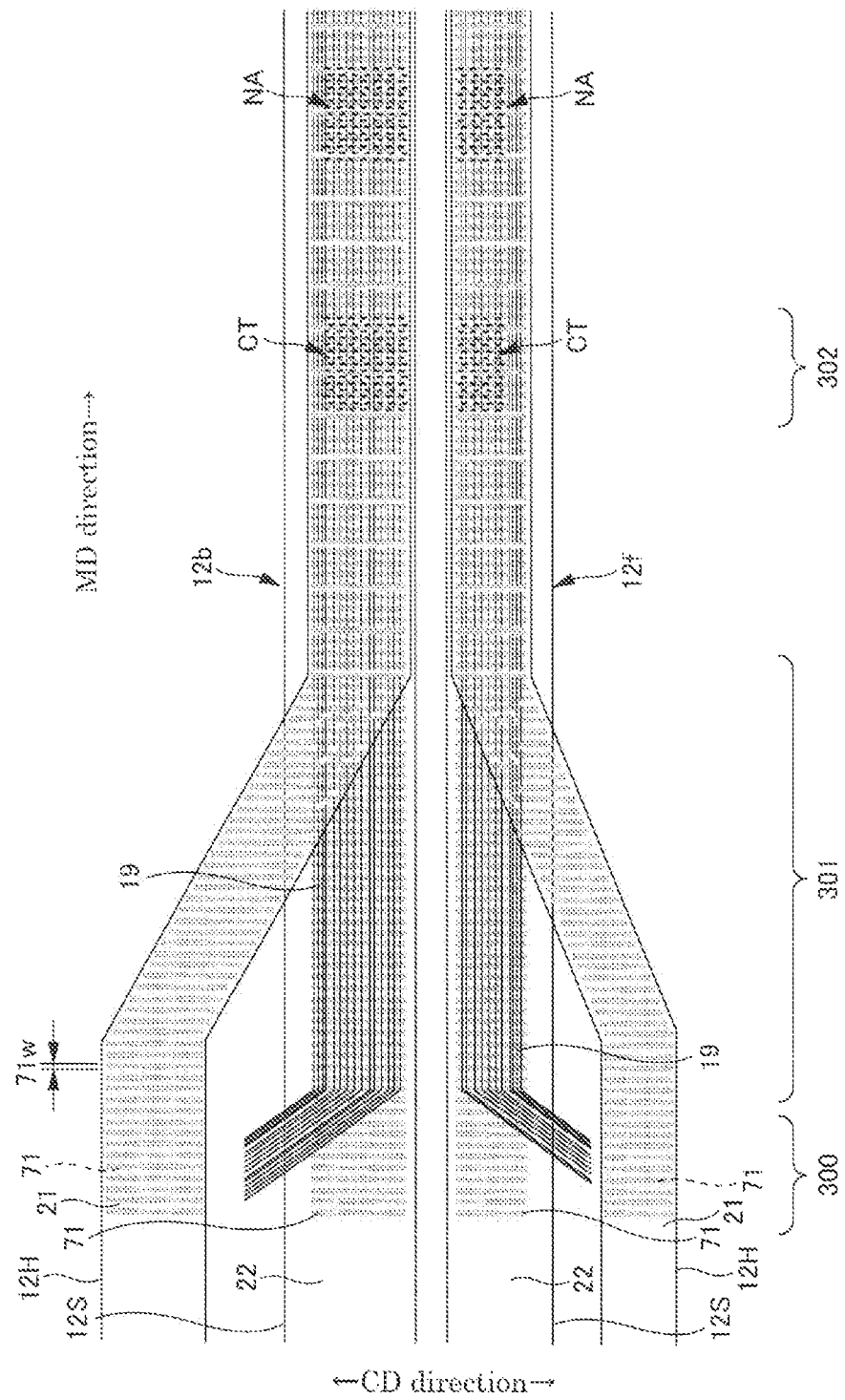
FIG. 13 is a planar view schematically illustrating production flow.
Figure 14:
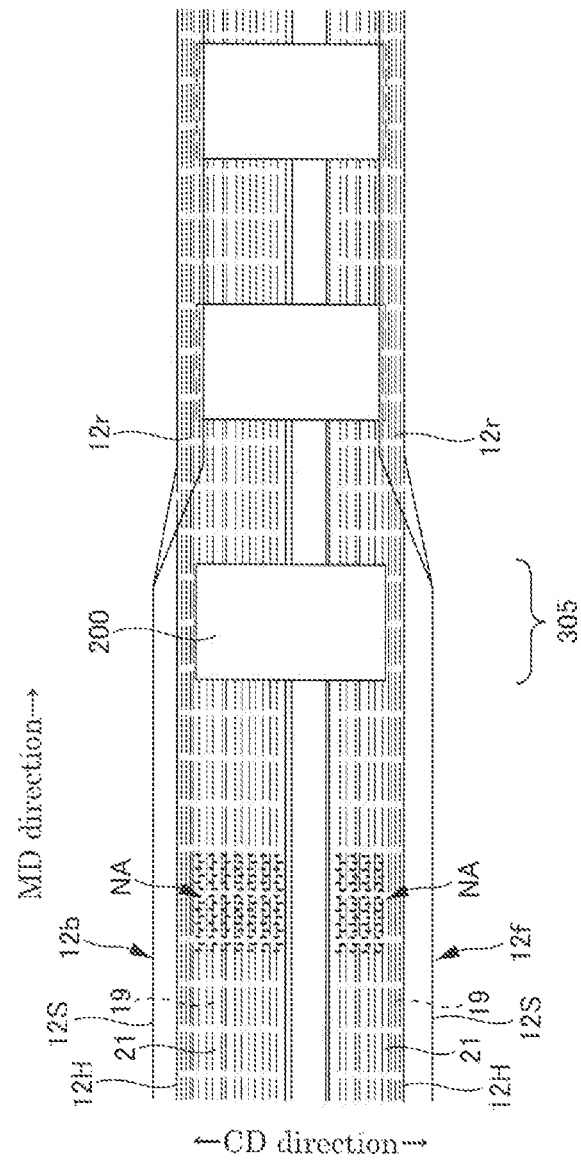
FIG. 14 is a planar view schematically illustrating the production flow.
Figure 15:
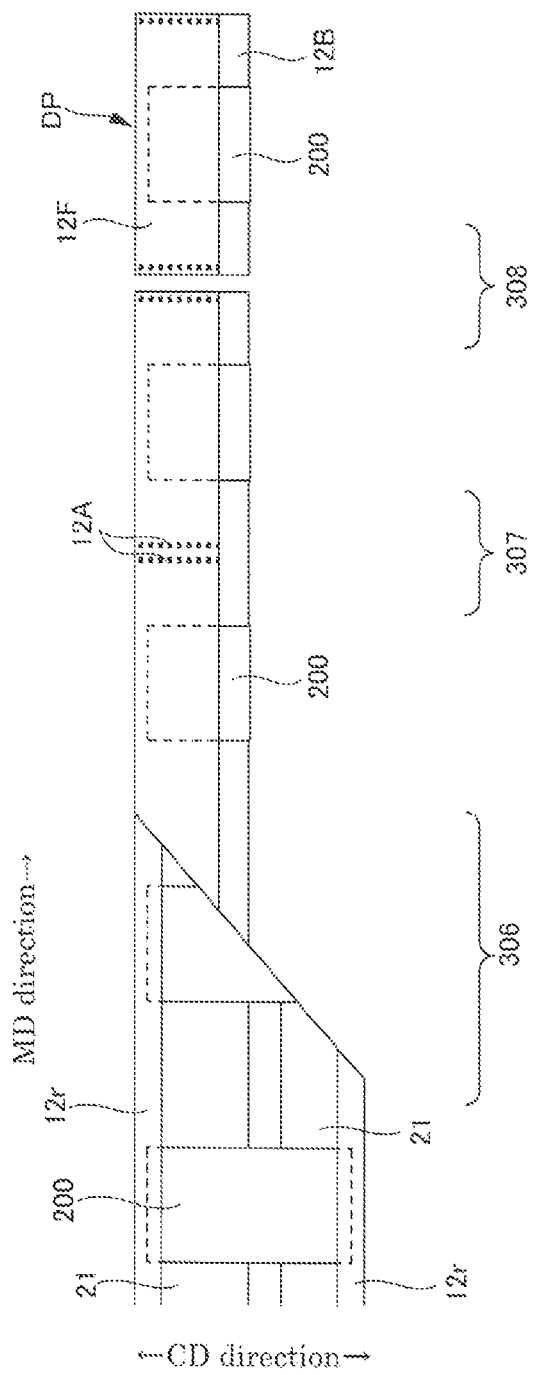
FIG. 15 is a planar view schematically illustrating the production flow.

FIGS. 13 to 15 illustrate an example of a method for producing an underpants-type disposable diaper. This production line is formed for a lateral flow with the diaper width direction in parallel to the MD direction (machine direction or line flow direction). In this line, a ventral side elastic belt 12f that is to be a ventral side outer body 12F and a dorsal side elastic belt 12b that is to be a dorsal side outer body 12B are formed, and an inner body 200 produced in another line is attached to the ventral side elastic belt 12f and the dorsal side elastic belt 12b. For the sake of ease of understanding, the continuous members in the production process are given the same reference signs as those of the members after the production.

To be more specific, this production line includes an adhesive application step 300, a resilient member attachment step 301, a resilient member cutting step 302, an inner body attachment step 305, a folding up step 306, a side part joining step 307, and a cutoff step 308. Among them, the steps from the adhesive application step 300 to the resilient member attachment step 301 are mainly characteristic in comparison with the conventional one.

That is to say, at the adhesive application step 300, the first sheet materials 12S (including the outside layers 22) and the second sheet materials 12H (inside layers 21) that are continuous in belt-shaped manner with predetermined widths for the ventral side outer body 12F and the dorsal side outer body 12B are supplied. Then, the adhesive 71 is applied to both the internal surfaces (upper surfaces in the drawings) of the outside layers 22 and the external surfaces (lower surfaces in the drawings) of the inside layers 21 in the same vertical striped pattern intermittent in the MD direction while continuously transporting the first sheet materials 12S and the second sheet materials 12H in the MD direction.

At the subsequent resilient member attachment step 301, the inside layers 21 and the outside layers 22 are bonded to each other such that the positions of the adhesive 71 on the inside layers 21 in the MD direction and the positions of the adhesive 71 on the outside layers 22 in the MD direction are made to match with each other and the large number of elongated resilient and elastic members 19 are continuously sandwiched between the inside layers 21 and the outside layers 22 in an extended state in the MD direction so as to be spaced from each other in the CD direction, thereby fixing the resilient and elastic members 19 to the inside layers 21 and the outside layers 22 with the adhesive 71. With this, a ventral side elastic belt 12f and a dorsal side elastic belt 12b that are continuous in the belt-shaped manner are formed. When the adhesive 71 is applied to both the opposing surfaces of the inside layers 21 and the outside layers 22 in the same vertical striped pattern and the inside layers 21 and the outside layers 22 are bonded to each other such that the positions of the adhesive 71 on both of them are made to match with each other as described above, the resilient and elastic members 19 are made to firmly adhere to both the inside layers 21 and the outside layers 22 in the portions intersecting with the adhesive 71.

The hot-melt adhesive 71 is preferably used as the adhesive 71 at the adhesive application step 300. As the hot-melt adhesive 71, for example, there are various adhesives based on EVA, adhesive rubber (elastomer), olefin, polyester and polyamide, and they can be used without specific limitation. Among them, the adhesive based on the adhesive rubber (elastomer) is desirably used. In order to perform positional adjustment easily when the inside layers 21 and the outside layers 22 are bonded each other or examine positional deviation and so on, a colored (except transparent and white) adhesive is used or an adhesive containing a fluorescent component is used as disclosed in JP 2003-145028 A, as a preferable form.

Figure 16:
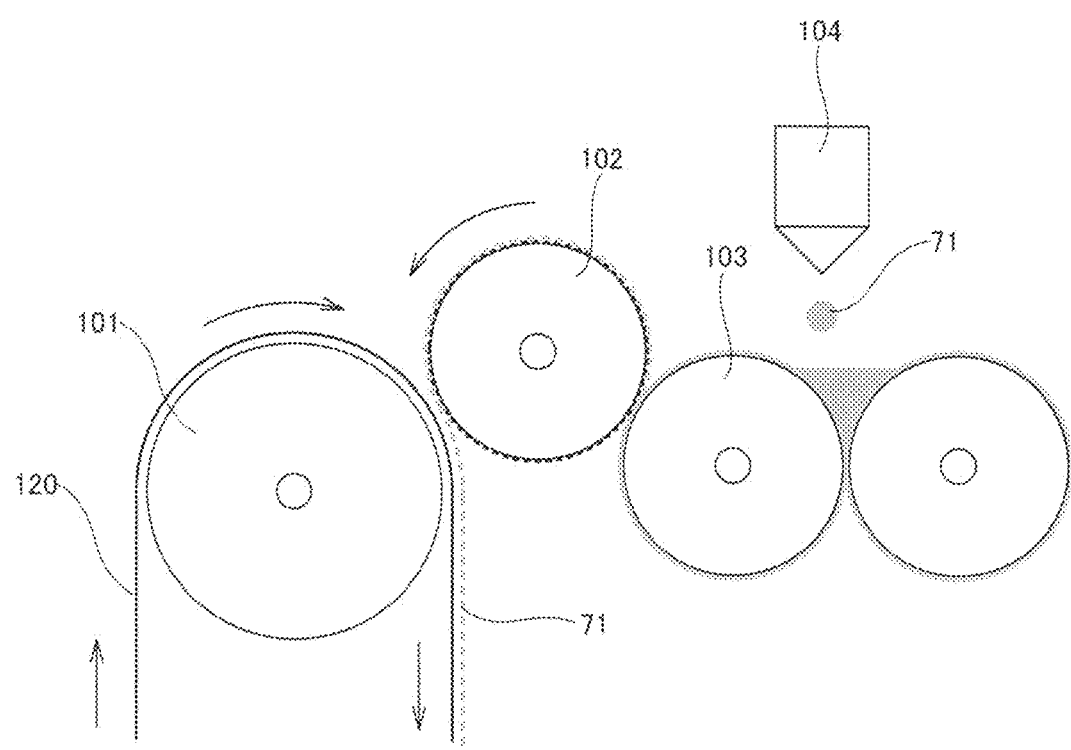
FIG. 16 is a schematic view of adhesion facility.

There is no specific limitation on an application method of the hot-melt adhesive 71. As described above, when the width 70w of each sheet joined section 70 is set to be as small as equal to or less than 1 mm, for example, the application width 71w of the hot-melt adhesive 71 is decreased and it is difficult to apply the hot-melt adhesive 71 by intermittent application using an application method of ejecting it from nozzles through curtain, solid, or the like. Accordingly, in such a case, a pattern coat (transfer of the hot-melt adhesive 71 with a relief printing method) preferable for application with the small width is desirably employed. FIG. 16 illustrates an example of pattern coat facility of the hot melt adhesive. That is to say, in this pattern coat facility, each sheet material 120 (the first sheet material 12S and the second sheet material 12H in the first embodiment) to be applied is made contact with a plate roll 102 having a convex pattern intermittent in the circumferential direction in a process of being guided along a roll 101, so that the hot-melt adhesive 71 is transferred and applied there onto intermittently in the transportation direction (MD direction, which corresponds to the width direction) and continuously in the direction (CD direction) intersecting with the transportation direction. A reference numeral 103 indicates a hot-melt adhesive supply roll (anilox roll in relief printing) for transferring and applying the hot-melt adhesive 71 to the convex pattern of the plate roll 102 with predetermined thickness and a reference numeral 104 indicates a supply nozzle for supplying the hot-melt adhesive 71 to the hot-melt adhesive supply roll 103.

Even when the application method by the foregoing pattern coat is employed, the hot-melt adhesive 71 may show stringiness depending on types of the hot-melt adhesive 71, resulting in a risk that accuracy of the application width (that is, the width of the sheet joined sections 70) is lowered or operation stability is lowered. For this reason, as the hot-melt adhesive 71, the hot-melt adhesive 71 having melt viscosity of equal to or lower than 10000 mpas at a temperature of 140° C. and melt viscosity of equal to or lower than 5000 mpas at a temperature of 160° C. and having loop tack adhesion of equal to or higher than 2000 g/25 mm is desirably used. This can reduce the risk of stringiness and improve the accuracy of the application width and the operation stability.

The loop tack adhesion of the hot-melt adhesive 71 refers to a value that is measured in the following manner. That is to say, the hot-melt adhesive is applied with the thickness of 50 μm onto a PET plate having the thickness of 50 μm. This is cut out into a size having the width of 25 mm and the length of 125 mm and is formed into a tape shape. After that, both ends of the tape are overlapped to form a loop shape. The loop is fixed to an LT-100-type loop tack tester (manufactured by Cheminstruments, Inc.), and then, is made to adhere to a polyethylene (PE) plate with the adhesion area of 25 mm×25 mm for the adhesion period of time of 2 seconds. Subsequently, the loop-shaped tape is stripped off at 20° C. at the stripping rate of 300 mm/min and maximum force is measured to be set to the loop tack adhesion.

Furthermore, the melt viscosity of the hot-melt adhesive 71 is measured at a defined temperature using a Brookfield B-type viscometer (spindle No. 027) in accordance with JIS Z 8803.

The elastic belts 12f and 12b formed through the resilient member attachment step 301 are subjected to the resilient member cutting step 302 if necessary before the inner body attachment step 305, which will be described later. Parts (parts forming the non-stretchable regions NA) of the resilient and elastic members 19 of the dorsal side elastic belt 12b and the resilient and elastic members 19 of the ventral side elastic belt 12f are finely divided in the width direction at predetermined intervals in the MD direction by a method such as cutting and heat embossing. The corresponding regions are the non-stretchable regions NA in which the contraction force of the resilient and elastic members 19 do not act. The resilient member cutting step 302 can be also omitted.

Thereafter, at the inner body attachment step 305, the inner bodies 200 that have been previously manufactured in another line are supplied at predetermined intervals in the MD direction. Front side parts of the inner bodies 200 are joined to the ventral side elastic belt 12f and dorsal side parts of the inner bodies 200 are joined to the dorsal side elastic belt 12b, thereby forming inner assembly bodies. The joining can be performed by appropriate means such as a hot-melt adhesive or heat seal. The inner bodies 200 that have been formed as complete bodies in another line may be supplied or a plurality of parts thereof formed in other lines may be individually supplied and assembled on the elastic bodies 12f and 12b.

At the inner body attachment step 305, after the inner bodies 200 are joined together to the internal surfaces of the elastic belts, the end portions of the first sheet materials 12S at the outer sides in the CD direction are folded back to the center side in the CD direction and regions to both the end portions of the inner bodies 200 in the CD direction are covered by the folded parts 12r of the first sheet materials 12S, as appropriate. The folded parts 12r are fixed to the internal surfaces of the second sheet materials 12H and the internal surfaces of both end portions of the inner bodies 200 in the CD direction by appropriate means such as the hot-melt adhesive 71 or the heat seal.

After the inner assembly bodies are folded back at the center in the CD direction such that the attachment surface of the ventral side elastic belt 12f for the inner bodies 200 and the attachment surface of the dorsal side elastic belt 12b for the inner bodies 200 overlap with each other at the folding up step 306, the ventral side elastic belt 12f and the dorsal side elastic belt 12b are joined together in portions corresponding to both the side portions of the individual diapers to form the side seal portions 12A at the side part joining step 307. Then, at the cutoff step 308, the ventral side elastic belt 12f and the dorsal side elastic belt 12b are cut at the boundaries of the respective diapers so as to provide individual diapers DP. The side part joining step 307 and the cutoff step 308 can be performed at the same time. When the width of the ventral side elastic belt 12f and the width of the dorsal side elastic belt 12b are not identical to each other, the side seal portions 12A may be formed on only portions in which both the elastic belts 12f and 12b overlap with each other or may be formed on the entire regions including extra portions formed on the wider belt.

Figure 17A:
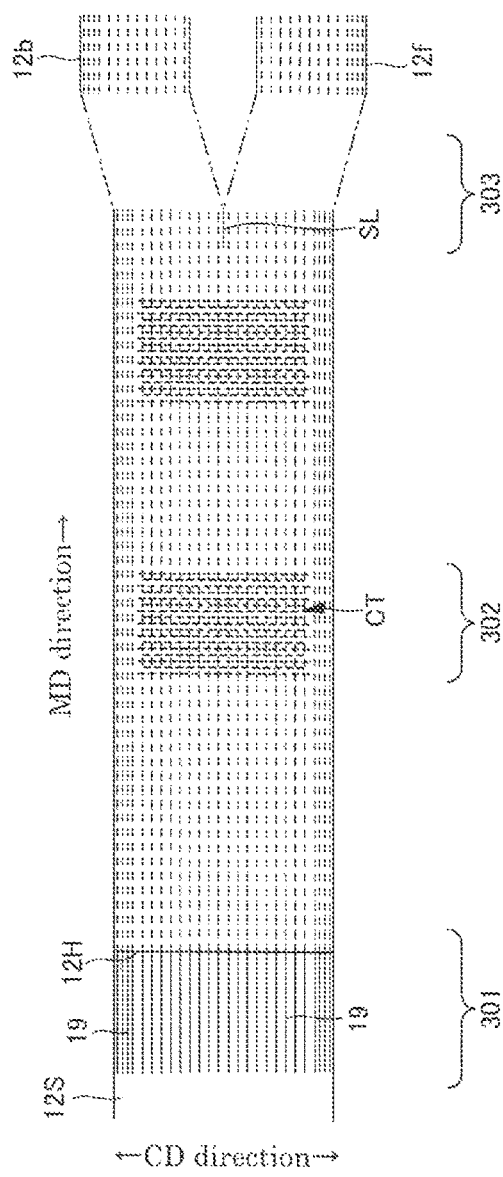
FIGS. 17 (a) and (b) are planar views schematically illustrating the production flow.
Figure 17B:
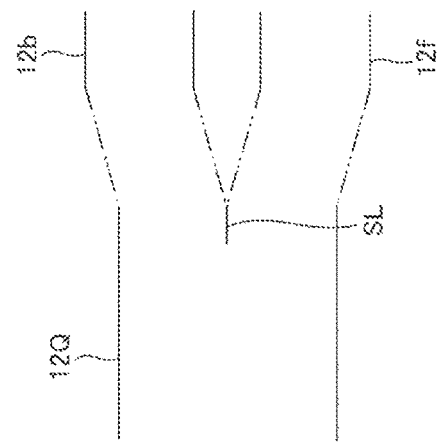

The above-mentioned production method enables an underpants-type disposable diaper same as that in the foregoing form illustrated in FIG. 1 to FIG. 7 to be manufactured. In the foregoing example, the sheet materials for the ventral side and the sheet materials for the dorsal side are separately supplied or formed and they are separately subjected to the adhesive application step 300 and the resilient member attachment step 301 so as to form the dorsal side elastic belt 12b and the ventral side elastic belt 12f individually. Alternatively, the following method for forming the ventral side elastic belt 12f and the dorsal side elastic belt 12b can be also employed. That is, as illustrated in FIG. 17(a), the first sheet material 12S and the second sheet material 12H having the widths for the amount of both the ventral side and the dorsal side are supplied to form one elastic belt. Thereafter, at a center slit cutting step 303, the elastic belt is divided at an intermediate position SL in the CD direction by a slitter to form the ventral side elastic belt 12f and the dorsal side elastic belt 12b. As illustrated in FIG. 17(b), the first sheet material 12S and the second sheet material 12H can be also formed by cutting one sheet material 12Q inline by the slitter at the intermediate position SL in the CD direction and supplied to the adhesive application step 300 as it is.

Second Embodiment

Figure 18:
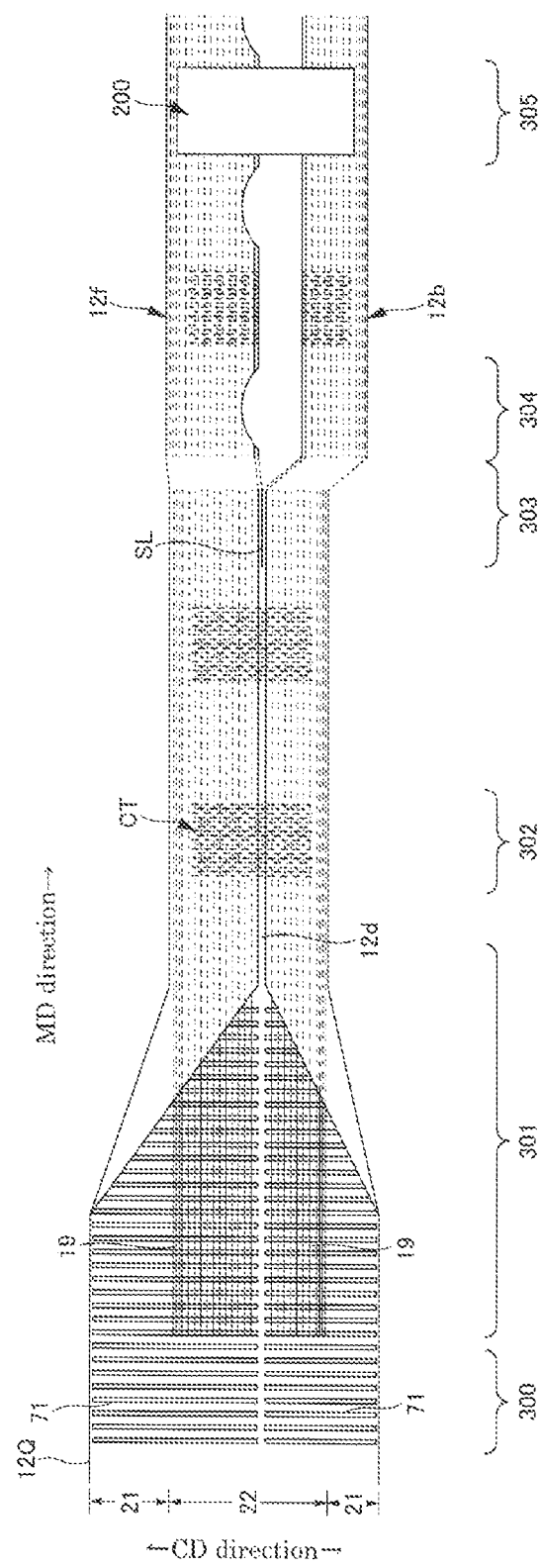
FIG. 18 is a planar view schematically illustrating the production flow.
Figure 19:
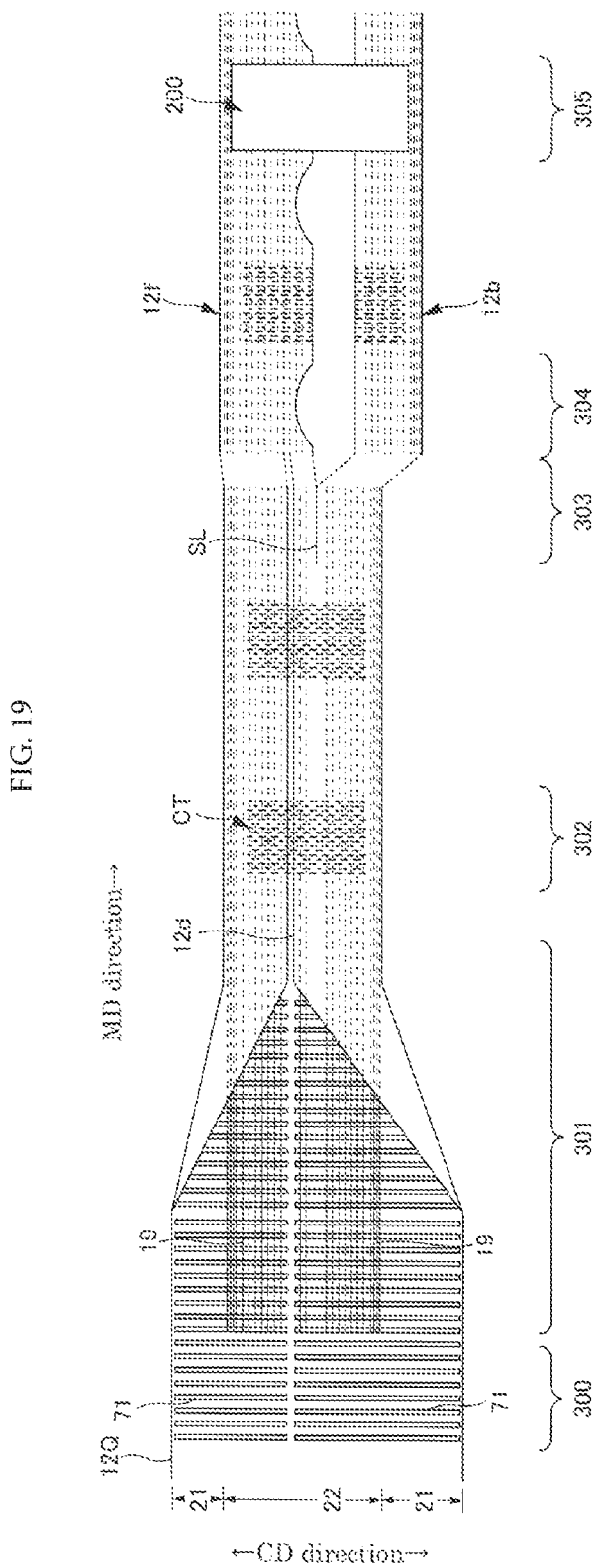
FIG. 19 is a planar view schematically illustrating the production flow.

As in the above-mentioned first embodiment, when the separate first sheet materials 12S and second sheet materials 12H as the inside layers 21 and the outside layers 22 are transported and bonded to each other, the positions of the adhesive 71 on the first sheet materials 12S in the MD direction and the positions of the adhesive 71 on the second sheet materials 12H in the MD direction are easy to be deviated and positional adjustment for matching the positions is complicated. In consideration of this, a second embodiment illustrated in FIG. 18 and FIG. 19 is also proposed. That is to say, the second embodiment is different from the first embodiment in a point that the center slit cutting step 303 is added between the resilient member cutting step 302 and the inner body attachment step 305 while changing the adhesive application step 300 and the resilient member attachment step 301.

To be more specific, at the adhesive application step 300, one sheet material 12Q continuous in a belt-shaped manner, which includes the inside layer 21 and the outside layer 22 of the ventral side outer body 12F and the outside layer 22 and the inside layer 21 of the dorsal side outer body 12B in this order from one side in the CD direction, is supplied, and the adhesive 71 is applied to the internal surface (upper surface in the drawings) thereof over both the inside layer 21 and the outside layer 22 of the ventral side outer body 12F in the vertical striped pattern and over both the inside layer 21 and the outside layer 22 of the dorsal side outer body 12B in the vertical striped pattern while transporting the sheet material 12Q along the continuous direction. The patterns of the inside layers 21 and the patterns of the outside layers 22 may be separated from each other as long as the vertical striped patterns having the same positions in the MD direction are formed on the positions on the inside layers 21 and the outside layers 22. As illustrated in FIG. 18 and FIG. 19, the vertical striped pattern of the adhesive 71 at the ventral side and the vertical striped pattern of the adhesive 71 at the dorsal side are separated from each other so as to correspond to the positions of the inside layers 21 at the resilient member attachment step 301 and subsequent steps, which will be described later. Alternatively, the vertical striped pattern of the adhesive 71 at the ventral side and the vertical striped pattern of the adhesive 71 at the dorsal side can be made to be continuous although not illustrated in the drawings.

At the subsequent resilient member attachment step 301, an elastic belt continuous in the belt-shaped manner is formed in the following manner. That is, a large number of resilient and elastic members 19 are supplied to portions of the outside layers 22 located at the intermediate positions of the sheet material 12Q in the CD direction in a state of being extended in the MD direction with spaces left therebetween in the CD direction. Then, a portion of the inside layer 21 of the ventral side outer body 12F, which is located at one side relative to the portions of the outside layers 22 located on the intermediate positions of the sheet material 12Q in the CD direction, and a portion of the inside layer 21 of the dorsal side outer body 12B, which is located at the other side relative to the portions of the outside layers 22, are folded back to the side of the resilient and elastic members 19 on the portions of the outside layers 22 located at the intermediate positions of the sheet material 12Q in the CD direction and are bonded to each other. The resilient and elastic members 19 are sandwiched between the inside layers 21 and the outside layers 22. Thus, the resilient and elastic members 19 are fixed to the inside layers 21 and the outside layers 22 with the adhesive 71, thereby forming the elastic belt. When the inside layers 21 and the outside layers 22, which are the one-side portions and the-other-side portions relative to the intermediate positions of the one continuous belt-shaped sheet material in the CD direction, are folded back in the CD direction and are bonded to each other after the application of the adhesive 71 as described above, the positions of the adhesive 71 on the inside layers 21 in the MD direction and the positions of the adhesive 71 on the outside layers 22 in the MD direction are less deviated (no positional deviation is generated at at least the fold side) even without positional adjustment (although the positional adjustment may be performed).

A folding manner of the sheet material 12S at the forgoing resilient member attachment step 301 is a folding manner (what-is-called C folding) by which the portions of the inside layers 21 at the one side and the other side relative to the portions of the outside layers 22 located at the intermediate positions of the sheet material 12S in the CD direction are folded back to the side of the resilient and elastic members 19 on the portions of the outside layers 22 at the intermediate positions in the CD direction. Therefore, the folding width of the sheet material 12S is extremely small and facility (sailor) for folding is therefore reduced in size, thereby easily folding it back neatly with no wrinkle. In a product state, as in the forms illustrated in FIGS. 8(*b*) to 8(*f*), both the waist edges of the ventral side outer body 12F and the dorsal side outer body 12B are folds of the sheet material 12S and texture and appearance of the waist edges are excellent. As illustrated in FIG. 18 and FIG. 19, the separation portion 12d in the forms illustrated in FIGS. 8(*b*) and 8(*c*) can be formed by separating the inside layers 21 at the one side and the other side in the CD direction from each other at the resilient member attachment step. Although not illustrated in the drawings, the overlapped portion 12w in the forms illustrated in FIGS. 8(*d*) to 8(*f*) can be formed by partially overlapping the end portions of the inside layers 21 at the one side and the other side in the CD direction with each other at the resilient member attachment step.

Subsequently, after the resilient member cutting step 302 is performed as necessary, at the center slit cutting step 303, the elastic belt is cut at a predetermined site SL at the intermediate position thereof in the CD direction by a slitter so as to be divided into the dorsal side elastic belt 12b and the ventral side elastic belt 12f and an interval between the dorsal side elastic belt 12b and the ventral side elastic belt 12f in the CD direction is enlarged to a predetermined distance. The slit position SL may be a position at the center of the elastic belt in the CD direction or a position deviated to the ventral side or the dorsal side. As in the general underpants-type disposable diaper, in order to make the dorsal side elastic belt 12b be vertically longer than the ventral side elastic belt 12f, the slit position SL is preferably deviated to the ventral side. When the slit position SL is located on the separation portion 12d as illustrated in FIG. 18, the form illustrated in FIG. 8(*b*) can be achieved. When the slit position SL is made to shift to the dorsal side relative to the separation portion 12d as illustrated in FIG. 19, the form illustrated in FIG. 8(*c*) can be achieved. The forms illustrated in FIGS. 8(*d*) to 8(*f*) can be achieved by forming the overlapped portion by partially overlapping the end portions of the inside layers 21 at the one side and the other side in the CD direction with each other and appropriately changing the slit position SL, and so on at the resilient member attachment step 301, although not illustrated in the drawings. A punching step 304 for cutting the leg side edge of the dorsal side outer body 12B into a curved shape around the legs may be added as necessary after the center slit cutting step 303 as in the form illustrated in the drawings. The punching step 304 can be performed after the resilient member attachment step 301 and before the cutoff step 308, but is preferably performed before the folding up step 306, and is more preferably performed before the inner body attachment step 305.

The example as illustrated in the drawings employs the method in which one elastic belt is assembled by one sheet material 12Q, and then, is divided so as to form the ventral side elastic belt 12f and the dorsal side elastic belt 12b. Alternatively, the following method can be also employed. That is, the sheet material for the ventral side and the sheet material for the back side are separately supplied or formed and they are separately subjected to the adhesive application step 300 and the resilient member attachment step 301 of forming the inside layers 21 and the outside layers 22 by folding so as to form the dorsal side elastic belt 12b and the ventral side elastic belt 12f individually. Other points including subsequent steps are the same as those in the first embodiment and description thereof is therefore omitted.

Third Embodiment

Figure 20:
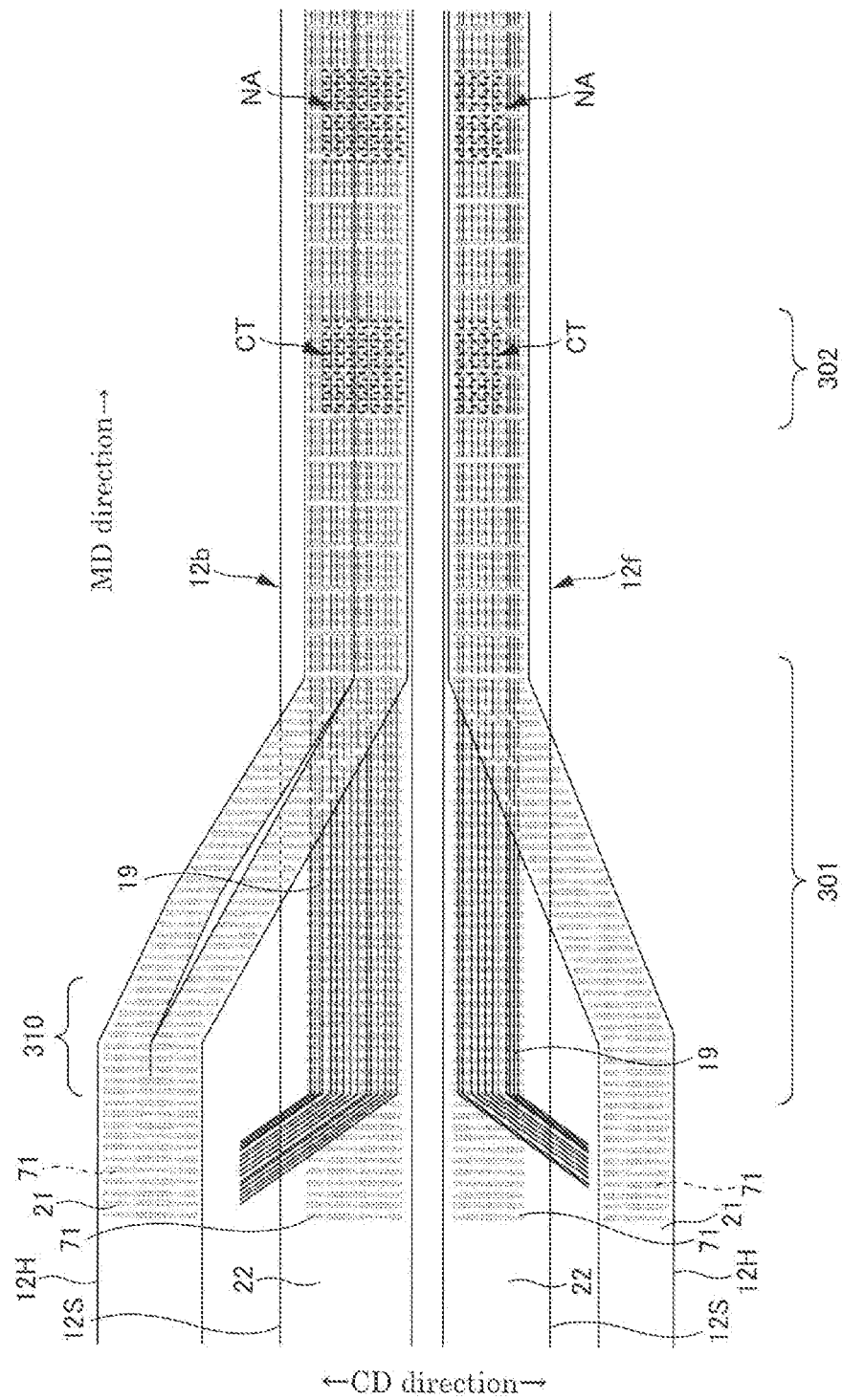
FIG. 20 is a planar view schematically illustrating the production flow.
Figure 22A:
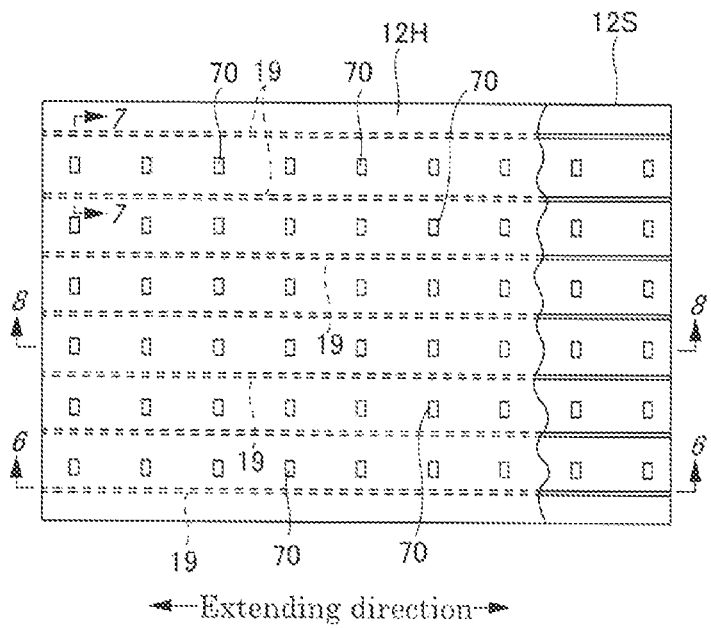
FIG. 22(a) is a planar view of a conventional stretchable structure in the open state.
Figure 22D:
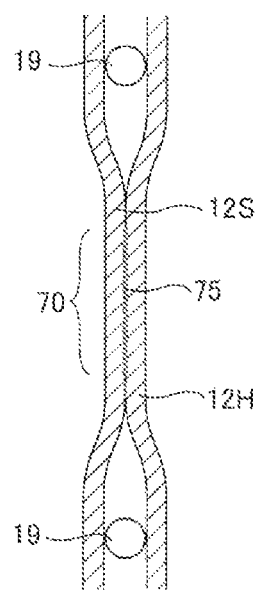
FIG. 22(b) is a cross-sectional view of the conventional stretchable structure taken along line 8-8 in the state of natural length, FIG. 22 (c) is a cross-sectional view of the conventional stretchable structure taken along line 6-6 in the state of natural length, and FIG. 22 (d) is a cross-sectional view of the conventional stretchable structure taken along line 7-7.
Figure 22B:
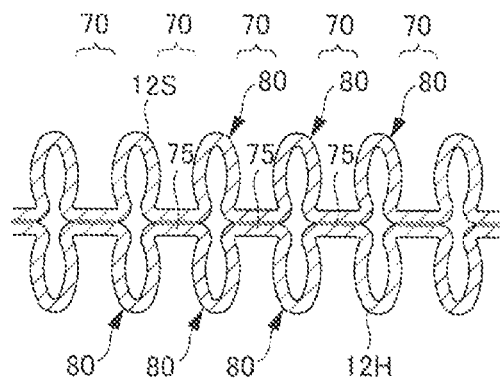
Figure 22C:
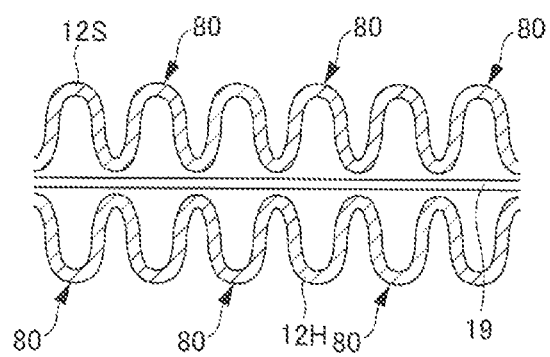

In general, in a production line for assembly while transporting a continuous belt-shaped sheet such as non-woven fabric, when the sheet width (length in the CD direction) is increased, it is difficult to adjust the position thereof in the MD direction entirely in the CD direction. Therefore, when the widths of the inside layers 21 and the outside layers 22 to be transported (the lengths in the CD direction) are large, it is difficult to adjust the positions of the adhesive 71 on the inside layers 21 in the MD direction and the positions of the adhesive 71 on the outside layers 22 in the MD direction entirely in the CD direction. For coping with this, the following is also one preferable form. That is, as illustrated in FIG. 20, the positions of the adhesive 71 on the inside layers 21 in the MD direction and the positions of the adhesive 71 on the outside layers 22 in the MD direction are made to match with each other by performing a division step 310 of dividing the inside layers 21 (may be the outside layers 22) into a plurality of portions at the intermediate positions in the CD direction by a slitter and individually adjusting the positions of these divided portions in the MD direction before the inside layers 21 and the outside layers 22 are bonded to each other. Thereafter, the inside layers 21 and the outside layers 22 are bonded to each other. By dividing any ones of the inside layers 21 and the outside layers 22 to decrease the widths thereof before the inside layers 21 and the outside layers 22 are bonded to each other as described above, the positional adjustment for matching the positions of the adhesive 71 on the inside layers 21 in the MD direction and the positions of the adhesive 71 on the outside layers 22 in the MD direction can be performed easily, thereby suppressing occurrence of positional deviation. The example illustrated in the drawing applies this positional adjustment method to formation of the dorsal side elastic belt 12b having a large width in the CD direction. Instead of or in addition to this, this positional adjustment method can be also applied to formation of the ventral side elastic belt 12f. Furthermore, this positional adjustment method can be also applied to the above-mentioned second embodiment.

Fourth Embodiment

Figure 23:
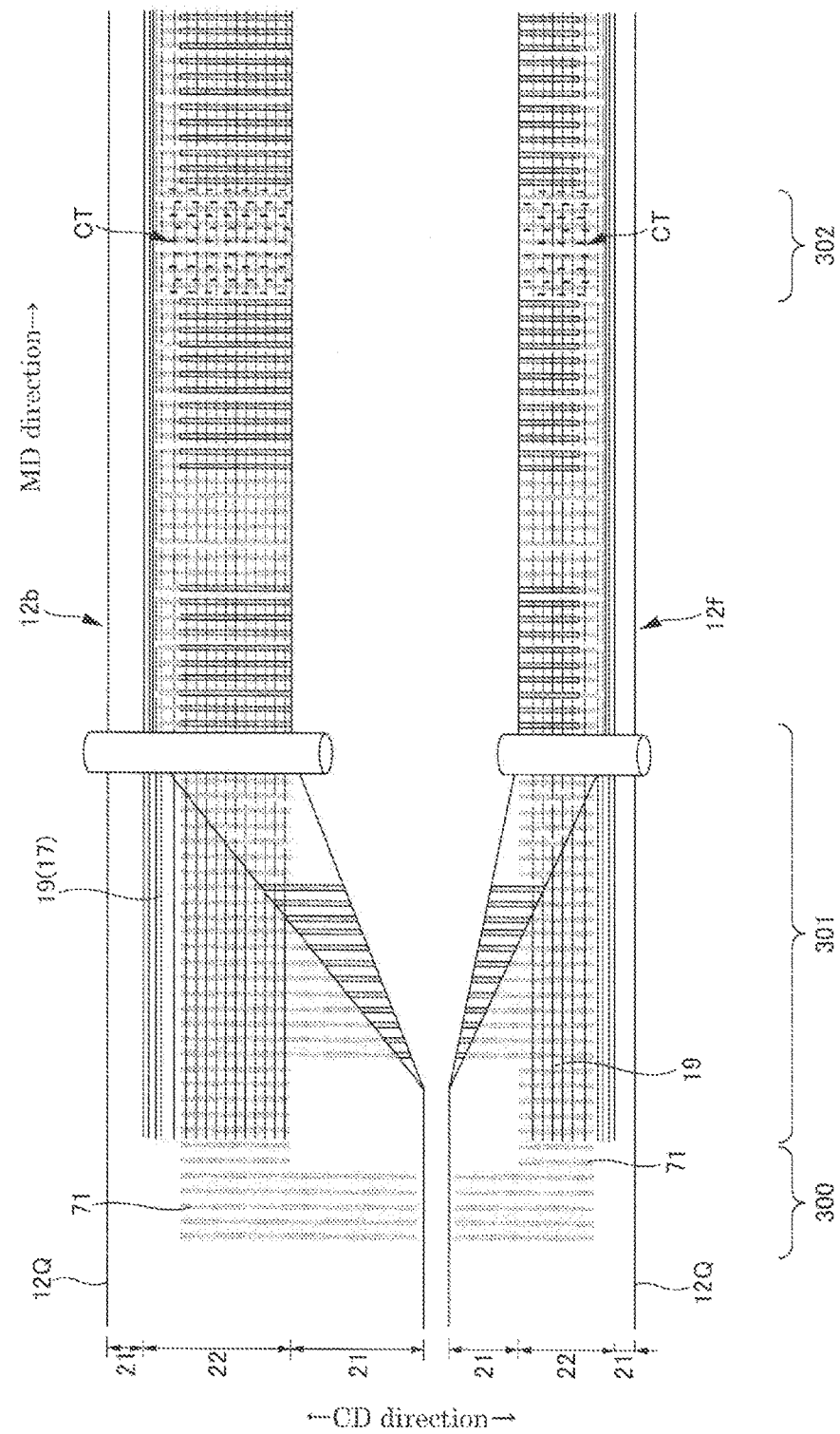
FIG. 23 is a planar view schematically illustrating production flow.

In case of forming of the stretchable regions by the resilient member cutting step 302, in order to produce an underpants-type disposable diaper in which the amount of the adhesive 71 in the foregoing non-stretchable regions NA is reduced, the following is also one preferable form. That is, as illustrated in FIG. 23, at the adhesive application step 300, the adhesive 71 is applied to both the external surfaces of the inside layers 21 and the internal surfaces of the outside layers 22 in the same vertical striped pattern intermittent in the MD direction at the sites corresponding to the stretchable regions while transporting the inside layers 21 and the outside layers 22 in the MD direction in the same manner as the first embodiment whereas the adhesive 71 is applied to any ones (the outside layers 21 in the form as illustrated in the drawing) of the external surfaces of the inside layers 21 and the internal surfaces of the outside layers 22 in the vertical striped pattern continuous from the stretchable regions and the adhesive 71 is not applied to the others (the inside layers 22 in the form as illustrated in the drawing) thereof at the sites corresponding to the non-stretchable regions NA (in other words, the adhesive 71 in the vertical striped pattern is not applied to any ones of the inside layers 21 and the outside layers 22 intermittently in the MD direction in the non-stretchable regions NA). When the one-sided application is performed only in the non-stretchable regions NA as described above, reduction in the usage amount of the adhesive 71 and improvement in flexibility of the non-stretchable regions NA of the outer body 12 can be achieved.

Figure 24:
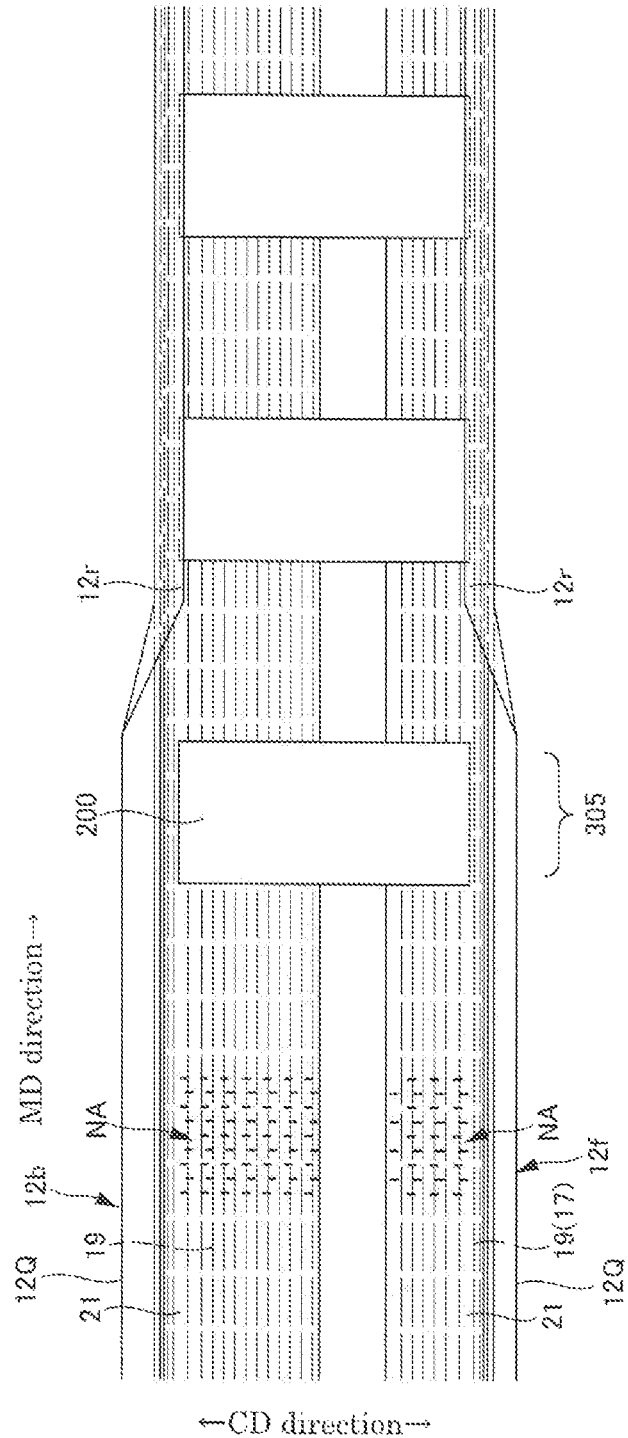
FIG. 24 is a planar view schematically illustrating the production flow.

Subsequently, it is sufficient that the resilient member attachment step 301, the resilient member cutting step 302, the inner body attachment step 305, the folding up step 306, the side part joining step 307, and the cutoff step 308 are performed in the same manner as the first embodiment. FIG. 24 illustrates the inner body attachment step 305 subsequent to the resilient member cutting step 302 illustrated in FIG. 23.

Fifth Embodiment

In case of forming of the stretchable regions by the resilient member cutting step 302, in order to produce the foregoing underpants-type disposable diaper excellent in the drawing preventing performance, the following is also one preferable form. That is, although not illustrated in the drawings, before the resilient member attachment step 301, the adhesive 71 is applied to the outer circumferential surfaces of the resilient and elastic members 19 in areas of the resilient and elastic members 19 in the MD direction, which correspond to both the end portions of the stretchable regions in the width direction. It should be noted that the adhesive 71 can be also applied to the outer circumferential surfaces of the resilient and elastic members 19 in areas of the resilient and elastic members 19 in the MD direction, which correspond to portions other than both the end portions of the stretchable regions, for example, the non-stretchable regions NA if necessary. However, the adhesive 71 is not applied to the outer circumferential surfaces of the resilient and elastic members 19 in areas in the MD direction, which correspond to portions between both the end portions of the stretchable regions. As a method for applying the adhesive 71 to the outer circumferential surfaces of the resilient and elastic members 19, a method using a sure-wrap nozzle, a method using a comb gun, or the like can be used.

Sixth Embodiment

When the underpants-type disposable diaper having the outer body 12 continuous from the ventral side to the back side through the crotch interposed therebetween as illustrated in FIG. 9 is produced, it is sufficient that one elastic belt having the width in the CD direction, which corresponds to the entire length of the diaper, is formed, a punching step of forming the leg openings is added, and the inner body attachment step 305 is executed without dividing the elastic belt at the intermediate position in the CD direction in the foregoing production method. The punching step can be executed after the resilient member attachment step 301 and before the cutoff step 308, but is preferably executed before the folding up step 306, and is more preferably executed before the inner body attachment step 305.

Seventh Embodiment

In the form in which the outer body is divided into two of the ventral side outer body 12F and the dorsal side outer body 12B, the ventral side elastic belt 12f serving as the ventral side outer body 12F and the dorsal side elastic belt 12b serving as the dorsal side outer body 12B can be formed in the following manner. That is, as in the form illustrated in FIG. 23 and FIG. 24, at the adhesive application step 300, one sheet material 12Q continuous in the belt-shaped manner, which includes portions forming the inside layer 21 and the outside layer 22 of the ventral side outer body 12F, and one sheet material 12Q continuous in the belt-shaped manner, which includes portions forming the outside layer 22 and the inside layer 21 of the dorsal side outer body 12B are supplied. Then, at the resilient member attachment step 301, both the sides (the crotch side and the waist side) of these sheet materials 12Q in the CD direction are folded back, thereby forming the ventral side elastic belt 12f serving as the ventral side outer body 12F and the dorsal side elastic belt 12b serving as the dorsal side outer body 12B.

Eighth Embodiment

The present invention encompasses the following form. That is, at the resilient member attachment step 301 in each of the above-mentioned forms, the position of the adhesive 71 on the inside layer 21 and the position of the adhesive 71 on the outside layer 22 are made to shift in the CD direction and one-sided application region is formed at one side of the double-sided application regions in the CD direction as long as the double-sided application region is formed. In particular, the following is also one preferable form. That is, as in the form illustrated in FIG. 23 and FIG. 24, the areas in the CD direction, which correspond to the sites for the non-stretchable regions NA, are formed as the double-sided application regions because the resilient and elastic members can be drawn whereas the areas in the CD direction, which do not correspond to the sites for the non-stretchable regions NA, are formed as the one-sided application regions because the resilient and elastic members are not drawn even when they are arranged in the areas. In the form illustrated in the drawings, the sites in which parts of the waist edge portion resilient and elastic members 17 are arranged are formed as the one-sided application regions. Alternatively, the sites in which all the waist edge portion resilient and elastic members 17 are arranged may be formed as the one-sided application regions or the sites in which the resilient and elastic members 19 are not arranged may be formed as the one-sided application regions. In any of the cases, when only the areas in the CD direction, which correspond to the sites for the non-stretchable regions NA, are formed as the double-sided application regions, the double-sided application regions can be narrowed in the CD direction. With this, the positional adjustment for matching the positions of the adhesive 71 on the inside layers 21 in the MD direction and the positions of the adhesive 71 on the outside layers 22 in the MD direction can be performed easily, thereby suppressing occurrence of positional deviation. This positional deviation prevention effect is further exerted when the ventral side elastic belt 12*f* serving as the ventral side outer body 12F and the dorsal side elastic belt 12*b* serving as the dorsal side outer body 12B are formed by the separate sheet materials as in the form illustrated in FIG. 23 and FIG. 24, or the like.

Experiment 1

Polypropylene fiber SSS non-woven fabric having fineness of 1.6 denier, basis weight of 17 g/m², thickness of 0.2 mm (initial thickness TO: thickness under the pressure of 0.5 g/cm²), bending resistance of 55 mm in the MD direction (direction of production line of the non-woven fabric), bending resistance of 28 mm in the CD direction (direction orthogonal to the MD direction) was cut to prepare a first sheet material and a second sheet material having length in the MD direction of 180 m and length in the CD direction of 40 mm. In addition, thread rubber of 470 dtex was prepared as a resilient and elastic member.

A hot-melt adhesive of width of 1 mm being continuous in the CD direction is applied with spacing of 7 mm onto a face of the first sheet material on the second sheet material side in the MD direction. Arranged thereon with spacing of 5 mm in the CD direction were seven rubber threads continuing in the MD direction and each in an extended state of 270%. Then, the second sheet material is arranged thereon aligning the MD direction and the CD direction with that of the first sheet material. The first sheet material, resilient and elastic members, and the second sheet material were placed on the face, and pressed and attached to prepare sample No. 1 of a stretch sheet. Note that natural length of this sample No. 1 in the MD direction was 67 mm. In addition, application width of the hot-melt adhesive was changed to 2 mm, 4 mm, 6 mm, and 10 mm, and application interval of the hot-melt adhesive was changed to 2 mm, 4 mm, 6 mm, 8 mm, and 10 mm, appropriately. Then, samples No. 2 to No. 13 were also prepared.

Formation status of the samples were observed and evaluated on zero-to-four scales. ◉: Pleats were formed very tidily; ○: Pleats were formed tidily; Δ: Pleats were formed but not tidily; x: Formation of pleats was not sufficient. The evaluation results were as listed in Table 1. Note that pleats were formed when the application interval of the hot-melt adhesive was 10 mm, but the pleats collapsed during compression because they were too large. The pleats were not formed when the application interval was 2 mm. In addition, when the application width of the hot-melt adhesive was 6 mm and 10 mm, the sheet joined sections also contracted, forming wrinkles.

TABLE 1

|  | No. 1 | No. 2 | No. 3 | No. 4 | No. 5 | No. 6 | No. 7 | No. 8 | No. 9 | No. 10 | No. 11 | No. 12 | No. 13 |
|---|---|---|---|---|---|---|---|---|---|---|---|---|---|
| Hot-melt adhesive application width (mm) | 1 | 2 | 2 | 2 | 4 | 4 | 2 | 2 | 6 | 6 | 6 | 10 | 10 |
| Hot-melt adhesive application interval (mm) | 7 | 4 | 6 | 8 | 4 | 6 | 2 | 10 | 2 | 4 | 6 | 6 | 10 |
| Pleat formation condition observation result | ◉ | ○ | ◉ | ◉ | ○ | ◉ | X | Δ | X | X | Δ | Δ | Δ |

◉: Pleats were formed very tidily
○: Pleats were formed tidily
Δ: Pleats were formed but not tidily
X: Formation of pleats was insufficient It can be seen from the results that desirable results can be obtained when the application width of the hot-melt adhesive (specifically, width direction dimension of the sheet joined section) is 0.5 to 4 mm and the application interval of the hot-melt adhesive (specifically, spacing between adjacent sheet joined sections) is 4 to 8 mm.

Experiment 2

Sample No. 14 of the stretch sheet was prepared in a manner similar to Experiment 1 (however, the application width of the hot-melt adhesive was 2 mm and the application interval was 6 mm).

Sample No. 15 was prepared in a manner similar to sample No. 14, except that a direction in which the hot-melt adhesive continues was the MD direction of the first sheet material and the second sheet material and a direction of rubber threads was the CD direction of the first sheet material and the second sheet material.

Then, in samples No. 14 and No. 15 of natural length, by aligning a center of a pressure plate, to be described below, with an apex position of the pleats for pleats at five locations, compression characteristics (compression stiffness LC, compression energy WC, compression resilience RC, initial thickness TO, thickness TM at maximum load) were measured, and averages were calculated. Note that the compression stiffness LC indicates that compression is rigid as it is closer to 1. The compression energy WC indicates that the larger the value is, the more easily the sample was compressed. The compression resilience RC indicates that the closer to 100 the value is, the better restorability to compression is. The initial thickness T0, the compression stiffness LC, the compression energy WC, and the compression resilience RC were measured using KES-FB3-AUTO-A automated compression tester based on KES (Kawabata's Evaluation System for Fabrics). Measurements took place during time from when a specimen was compressed between steel pressure plates having a circular plane of compression area of 2 cm$^2$ from 0 gf/cm$^2$ to the maximum compression load 50 gf/cm$^2$, till the specimen was restored. The initial thickness T0 is thickness of the specimen at pressure of 0.5 gf/cm$^2$. The compression stiffness LC represents linearity of compression displacement, and a specimen whose load and displacement (decrease in thickness due to compression) are proportional has a large value. The compression energy WC represents workload of compression, and the larger a numeric value is, the better fullness and stiffness are. The compression resilience represents compression resilience. Further, the larger a value is, the smaller hysteresis is.

TABLE 2

|  |  | Sample No. 14 | Sample No. 15 |
|---|---|---|---|
| LC | (—) | 1.15 | 0.91 |
| WC | (gfcm/cm$^2$) | 1.63 | 2.00 |
| RC | (%) | 53.3 | 42.7 |
| T0 | (mm) | 6.44 | 6.18 |
| TM | (mm) | 3.60 | 1.78 |
| T0-TM | (mm) | 2.83 | 4.40 |
| INT | (—) | 16.3 | 20.0 |
| B-INT | (—) | 8.68 | 8.54 |
| GAP | (mm) | 7.02 | 6.62 |

In addition, these samples No. 14 and No. 15 in a state in which they were stretched 1.65 times in the MD direction (assuming a state in which the diaper is attached) were microscope photographed from sides (magnification of 30 times). Based on the photograph results, apparent height 80Y and width 80X of the sample pleats were measured for each pleat 80 to calculate averages. FIG. 21 illustrates photographs and table 3 shows the pleat height and width. KEYENCE digital microscope VHX-1000 was used in the microscope shooting.

TABLE 3

|  |  | Sample No. 14 | Sample No. 15 |
|---|---|---|---|
| Height | (μm) | 4637 | 4467 |
| Width | (μm) | 3734 | 3008 |

It can be seen from these results that when bending resistance of non-woven fabric in the width direction is set higher than that in the direction orthogonal to the width direction, the pleats not only easily swell roundly and have rich compression resilience in the thickness direction, but also do not easily lie down and yet have softness when touched.

Experiment 3

The same first sheet material, the resilient and elastic members, and the second sheet material as Experiment 1 as well as various types of hot-melt adhesives that differ in the melt viscosity and loop tack adhesion were prepared. In equipment similar to that illustrated in FIG. 13, an adhesion test was carried out at line speed of 187 m/min to evaluate operation stability such as stringiness of the hot-melt adhesives or the like on the following two scales:

○: No stringiness was observed and bonding was carried out in a stable manner.

x: Stringiness was observed, precision of the application width was poor, and there was a problem in terms of the operation stability.

TABLE 4

|  |  | Type of hot-melt adhesive | | | | |
|---|---|---|---|---|---|---|
|  |  | A | B | C | D | E |
| Melt viscosity | 140 °C. | 4030 | 6030 | 6900 | 17500 | 21500 |
| (mpas) | 160 °C. | 1750 | 2950 | 3000 | 7080 | 8100 |
| Loop tack | (g/25 mm) | 2710 | 2550 | 1560 | 980 | 40 |
| Evaluation |  | ○ | ○ | X | X | X |

It can be seen from the results that desirable results can be obtained if a hot-melt adhesive having the melt viscosity of 10000 mpas or less at temperature of 140° C. and the melt viscosity of 5000 mpass or less at temperature of 160° C., and the loop tack adhesion of 2000 g/25 mm or more is used.

<Descriptions of the Terms Used Herein>

Unless otherwise specified herein, the terms used herein have the meanings as described below.

(Extension Ratio)

The extension ratio refers to a value with respect to 100% representing the natural length.

(Basis Weight)

The basis weight is measured as described below. A specimen or a test piece is preliminarily dried and left stand in a test room or a test device in a standard state (a place of test shall be at a temperature of 20±5° C. and a relative humidity of 65% or less) until reaching a constant weight. The preliminary drying refers to turning the specimen or the test piece to a constant weight in an environment at a relative humidity of 10 to 25% and a temperature not exceeding 50° C. The preliminary drying is not necessary for fibers with an official moisture regain of 0.0%. The test piece of the constant weight is cut into a 200 mm×250 mm (±2 mm) specimen by the use of a basis weight plate (200 mm×250 mm 2 mm). The weight of the specimen is measured and the measured value is multiplied by 20 to determine the weight per square meter as a basis weight.

(Thickness)

The thickness is automatically measured by an automated thickness gauge (KES-G5 handy compression measurement program) on the conditions that the load is 10 gf/cm$^2$ and the pressure area is 2 cm$^2$.

(Condition in Measurement)

If there is no description on environmental conditions in testing or measurements, the testing or the measurements shall be conducted in a test room or within a device under a normal state (a place of test shall be at temperatures of 20±5° C. and relative humidity of 60% or less).

INDUSTRIAL APPLICABILITY

The foregoing examples are suited to underpants-type disposable diapers but the method for producing the stretchable structure in the foregoing stretchable regions is also applicable to stretchable portions of other absorbent articles such as a waist portion and three-dimensional gather of a tape-type disposable diaper (the above-mentioned inside layer 21 and outside layer 22 correspond to a first layer and a second layer in the method for producing the stretchable structure of the absorbent article according to the invention, respectively).

REFERENCE SIGNS LIST

NA Non-stretchable region
11 Liquid impervious sheet
12 Outer body
12A Side seal portion
12B Dorsal side outer body
12F Ventral side outer body
12H Second sheet material
12S First sheet material
12b Dorsal side elastic belt
12f Ventral side elastic belt
12r Folded part
15, 18 Lower waist portion resilient and elastic member
16 Intermediate portion resilient and elastic member
17 Waist edge portion resilient and elastic member
19 Resilient and elastic member
21 Inside layer
22 Outside layer
30 Top sheet
40 Intermediate sheet
50 Absorbent element
56 Absorber
58 Wrapping sheet
60 Three-dimensional gather
62 Gather sheet
70 Sheet joined section
71 Adhesive
80 Pleat
200 Inner body
300 Adhesive application step
301 Resilient member attachment step
302 Resilient member cutting step
305 Inner body attachment step
306 Folding up step
307 Side part joining step
308 Cutoff step

The invention claimed is:

1. A method for producing a stretchable structure of an absorbent article,
the stretchable structure including a plurality of elongated resilient and elastic members provided with spaces left therebetween along an extending direction, and a first layer and a second layer facing one side and the other side of the resilient and elastic members, respectively, wherein
the first layer and the second layer are joined together with an adhesive applied in a striped pattern intermittent in the extending direction so as to form sheet joined sections,
the resilient and elastic members are fixed to the first layer and the second layer with the adhesive at positions intersecting with the sheet joined sections, and
the first layer and the second layer contract with contraction of the resilient and elastic members and portions of the first layer and the second layer between the sheet joined sections swell to directions opposite to each other so as to form pleats, the method comprising:
applying the adhesive to both an external surface of the first layer and an internal surface of the second layer in the same striped pattern intermittent in an MD direction while transporting the first layer and the second layer in the MD direction, and then, fixing the resilient and elastic members to the first layer and the second layer by bonding the first layer and the second layer to each other such that a position of the adhesive on the first layer in the MD direction and a position of the adhesive on the second layer in the MD direction are made to match with each other and sandwiching the resilient and elastic members between the first layer and the second layer continuously along the MD direction,
wherein the position of the adhesive on the first layer in the MD direction and the position of the adhesive on the second layer in the MD direction are made to match with each other by dividing any one of the first layer and the second layer into a plurality of portions at intermediate positions in the CD direction and individually adjusting positions of these divided portions in the MD direction before the first layer and the second layer are bonded to each other.

2. The method for producing the stretchable structure of the absorbent article according to claim 1, wherein
the first layer and the second layer are a one-side portion and another-side portion of one continuous belt-shaped sheet material, which is transported in the MD direction, relative to an intermediate position in a CD direction, and
the adhesive is applied to both the external surface of the first layer and the internal surface of the second layer in the striped pattern such that the positions of the adhesive in the MD direction are the same, and then, the resilient and elastic members are fixed to the first layer and the second layer with the adhesive by folding back the sheet material in the CD direction to bond the first layer and the second layer to each other and sandwiching the resilient and elastic members between the first layer and the second layer.

3. A method for producing an underpants-type disposable diaper,
the underpants-type disposable diaper including an outer body constituting a front panel and a back panel and an inner body having an absorber and fixed to an internal surface of the outer body, wherein
both side portions of the outer body in the front panel and both side portions of the outer body in the back panel are joined together to form side seal portions, thereby forming a waist opening and a pair of right and left leg openings, and
the outer body in at least one of the front and back panels includes an elongated resilient and elastic member along a width direction, an inside layer and an outside layer facing an inner side and an outer side of the resilient and elastic member, respectively, and sheet joined sections formed by joining the inside layer and the outside layer together with an adhesive applied in a vertical striped pattern intermittent in the width direction, and has stretchable regions in which the resilient and elastic member is fixed between the inside layer and the outside layer with the adhesive in portions intersecting with the sheet joined sections in a state of being extended in the width direction, and
in the stretchable regions, the inside layer and the outside layer contract with contraction of the resilient and elastic member, so that portions of the inside layer and the outside layer, which are located between the sheet joined sections, swell to directions opposite to each other so as to form pleats, the method comprising:

in forming the stretchable regions, applying the adhesive to both an external surface of the inside layer and an internal surface of the outside layer in the same vertical striped pattern intermittent in an MD direction while transporting the inside layer and the outside layer in the MD direction, and then, fixing the resilient and elastic member to the inside layer and the outside layer with the adhesive by bonding the inside layer and the outside layer to each other such that a position of the adhesive on the inside layer in the MD direction and a position of the adhesive on the outside layer in the MD direction are made to match with each other and sandwiching the resilient and elastic member between the inside layer and the outside layer continuously along the MD direction, wherein the position of the adhesive on the inside layer in the MD direction and the position of the adhesive on the outside layer in the MD direction are made to match with each other by dividing any one of the inside layer and the outside layer into a plurality of portions at intermediate positions in the CD direction and individually adjusting positions of these divided portions in the MD direction before the inside layer and the outside layer are bonded to each other.

4. The method for producing the underpants-type disposable diaper according to claim 3, wherein the underpants-type disposable diaper has a non-stretchable region formed in a region for fixing the inner body in the outer body, the stretchable regions are provided at respective sites between the non-stretchable region and the side seal portions at both sides in the width direction, and the inside layer and the outside layer are continuous from the stretchable region at one side in the width direction to the stretchable region at the other side through the non-stretchable region, in forming the stretchable regions and the non-stretchable region, the adhesive is applied to both the external surface of the inside layer and the internal surface of the outside layer in the same vertical striped pattern intermittent in the MD direction at sites corresponding to the stretchable regions while transporting the inside layer and the outside layer in the MD direction whereas the adhesive is applied to any one of the external surface of the inside layer and the internal surface of the outside layer in the vertical striped pattern continuous from the stretchable regions and the adhesive is not applied to the other of the external surface of the inside layer and the internal surface of the outside layer in the vertical striped pattern at a site corresponding to the non-stretchable region, and then, the resilient and elastic member is fixed to the inside layer and the outside layer with the adhesive by bonding the inside layer and the outside layer to each other such that the position of the adhesive on the inside layer in the MD direction and the position of the adhesive on the outside layer in the MD direction at the sites corresponding to the stretchable regions are made to match with each other and sandwiching the resilient and elastic member between the inside layer and the outside layer continuously along the MD direction, and subsequently, the resilient and elastic member only at the site corresponding to the non-stretchable region is finely cut in the MD direction.

5. The method for producing the underpants-type disposable diaper according to claim 4, wherein before the resilient and elastic member is sandwiched between the inside layer and the outside layer continuously along the MD direction, the adhesive is applied to an outer circumferential surface of the resilient and elastic member in areas of the resilient and elastic member in the MD direction, which correspond to both end portions of the stretchable regions in the width direction.

* * * * *